US012796927B2

(12) United States Patent
Ruppersberg

(10) Patent No.: US 12,796,927 B2
(45) **Date of Patent: *Nov. 17, 2026**

(54) SYSTEMS, DEVICES, COMPONENTS AND METHODS FOR DETECTING THE LOCATIONS OF SOURCES OF CARDIAC RHYTHM DISORDERS IN A PATIENT'S HEART

(71) Applicant: Boston Scientific Scimed, Inc., Maple Grove, MN (US)

(72) Inventor: Peter Ruppersberg, Blonay (CH)

(73) Assignee: Boston Scientific Scimed, Inc., Maple Grove, MN (US)

( * ) Notice: Subject to any disclaimer, the term of this patent is extended or adjusted under 35 U.S.C. 154(b) by 81 days.

This patent is subject to a terminal disclaimer.

(21) Appl. No.: 18/511,832

(22) Filed: Nov. 16, 2023

(65) Prior Publication Data

US 2024/0206731 A1 Jun. 27, 2024

Related U.S. Application Data

(63) Continuation of application No. 17/212,789, filed on Mar. 25, 2021, now Pat. No. 11,839,445, which is a (Continued)

(30) Foreign Application Priority Data

Sep. 7, 2015 (WO) ................. PCT/EP2015/001801
Sep. 7, 2015 (WO) ................. PCT/EP2015/001803

(51) Int. Cl.
*A61B 5/346* (2021.01)
*A61B 5/00* (2006.01)

(Continued)

(52) U.S. Cl.
CPC ............ *A61B 5/0006* (2013.01); *A61B 5/287* (2021.01); *A61B 5/327* (2021.01); *A61B 5/339* (2021.01);

(Continued)

(58) Field of Classification Search
CPC .. A61B 18/1492; A61B 5/6858; A61B 5/6852
See application file for complete search history.

(56) References Cited

U.S. PATENT DOCUMENTS 930,236 A 8/1909 Schacht
987,217 A 3/1911 Connor et al.

(Continued)

FOREIGN PATENT DOCUMENTS

CN 111655130 A 9/2020
EP 2586363 A1 5/2013

(Continued)

OTHER PUBLICATIONS

Intention to grant received for European Patent Application No. 21202891.4, mailed on May 26, 2025, 6 pages.

(Continued)

*Primary Examiner* — Eric D. Bertram
(74) *Attorney, Agent, or Firm* — Nelson Mullins Riley & Scarborough LLP

(57) ABSTRACT

Disclosed are various examples and embodiments of systems, devices, components and methods configured to detect a location of a source of at least one cardiac rhythm disorder in a patient's heart. In some embodiments, electrogram signals are acquired from inside a patient's heart, and subsequently normalized, adjusted and/or filtered, followed by generating a two-dimensional (2D) spatial map, grid or representation of the electrode positions, processing the amplitude-adjusted and filtered electrogram signals to generate a plurality of three-dimensional electrogram surfaces (Continued)

corresponding at least partially to the 2 D grid, one surface being generated for each of selected discrete times, and processing the plurality of three-dimensional electrogram surfaces through time to generate a velocity vector map corresponding at least partially to the 2 D grid. The resulting velocity vector map is configured to reveal the location of the source of the at least one cardiac rhythm disorder, which may be, by way of example, an active rotor in a patient's myocardium and atrium.

38 Claims, 22 Drawing Sheets

Related U.S. Application Data continuation of application No. 16/231,883, filed on Dec. 24, 2018, now Pat. No. 10,980,418, which is a continuation of application No. 15/548,671, filed as application No. PCT/IB2016/001273 on Sep. 7, 2016, now Pat. No. 10,201,277.

(51) Int. Cl.

*A61B 5/287* (2021.01)
*A61B 5/327* (2021.01)
*A61B 5/339* (2021.01)
*A61B 5/341* (2021.01)
*A61B 5/367* (2021.01)
*A61B 18/14* (2006.01)
*A61B 18/00* (2006.01)
*A61B 90/00* (2016.01)

(52) U.S. Cl.

CPC .............. *A61B 5/341* (2021.01); *A61B 5/346* (2021.01); *A61B 5/367* (2021.01); *A61B 5/6852* (2013.01); *A61B 5/6858* (2013.01); *A61B 5/742* (2013.01); *A61B 18/1492* (2013.01); *A61B 2018/00267* (2013.01); *A61B 2018/00351* (2013.01); *A61B 2018/00577* (2013.01); *A61B 2018/1467* (2013.01); *A61B 2090/065* (2016.02)

(56) References Cited

U.S. PATENT DOCUMENTS 1,684,880 A 9/1928 Norton
1,972,114 A 9/1934 Stephenson
2,042,372 A 5/1936 Watson
2,056,018 A 9/1936 Popp
4,186,451 A 2/1980 Ruo
4,622,702 A 11/1986 Allen
4,745,641 A 5/1988 Tash
5,172,699 A 12/1992 Svenson et al.
5,239,708 A 8/1993 Irwin
5,271,411 A 12/1993 Ripley et al.
5,383,917 A 1/1995 Desai et al.
5,427,112 A 6/1995 Noren et al.
5,433,196 A 7/1995 Fiat
5,433,198 A 7/1995 Desai
5,450,846 A 9/1995 Goldreyer
5,480,422 A 1/1996 Ben-Haim
5,487,391 A 1/1996 Panescu
5,549,108 A 8/1996 Edwards et al.
5,582,173 A 12/1996 Li
5,595,183 A 1/1997 Swanson et al.
5,609,158 A 3/1997 Chan
5,617,134 A 4/1997 Lamothe
5,657,755 A 8/1997 Desai
5,662,108 A 9/1997 Budd et al.
5,687,737 A 11/1997 Branham et al.
5,718,241 A 2/1998 Ben-Haim et al.
5,752,518 A 5/1998 McGee et al.
5,795,303 A 8/1998 Swanson et al.
5,817,134 A 10/1998 Greenhut et al.
5,840,025 A 11/1998 Ben-Haim
5,848,972 A 12/1998 Triedman et al.
5,868,680 A 2/1999 Steiner et al.
5,954,665 A 9/1999 Ben-Haim
6,052,618 A 4/2000 Dahlke et al.
6,066,094 A 5/2000 Ben-Haim
6,067,668 A 5/2000 Rudd
6,115,628 A 9/2000 Stadler et al.
6,188,924 B1 2/2001 Swanson et al.
6,236,883 B1 5/2001 Ciaccio et al.
6,256,540 B1 7/2001 Panescu et al.
6,301,496 B1 * 10/2001 Reisfeld ................. A61B 5/287 600/407
6,360,121 B1 3/2002 Shoda et al.
6,393,626 B1 5/2002 Dhillon
6,434,760 B1 8/2002 Montalvo
6,480,615 B1 11/2002 Sun et al.
6,480,815 B1 11/2002 Olson et al.
6,522,905 B2 2/2003 Desai
6,550,074 B1 4/2003 Allenbaugh et al.
6,584,345 B2 6/2003 Govari
6,684,417 B1 2/2004 Schneider
6,725,085 B2 4/2004 Schwartzman et al.
6,847,839 B2 1/2005 Ciaccio et al.
6,856,830 B2 2/2005 He
6,892,091 B1 5/2005 Ben-Haim et al.
6,920,350 B2 7/2005 Xue et al.
6,941,166 B2 9/2005 Macadam et al.
6,959,212 B2 10/2005 Hsu et al.
6,975,900 B2 12/2005 Rudy et al.
6,978,168 B2 12/2005 Beatty et al.
7,016,719 B2 3/2006 Rudy et al.
7,043,292 B2 5/2006 Tarjan et al.
7,081,114 B2 7/2006 Rashidi
7,117,030 B2 10/2006 Berenfeld et al.
7,123,954 B2 10/2006 Narayan et al.
7,206,630 B1 4/2007 Tarler
7,245,962 B2 7/2007 Ciaccio et al.
7,263,397 B2 8/2007 Hauck et al.
7,283,665 B2 10/2007 Suzuki
7,283,865 B2 10/2007 Noren
7,289,843 B2 10/2007 Beatty et al.
7,328,063 B2 2/2008 Zhang et al.
7,340,783 B2 3/2008 Leaphart et al.
7,505,810 B2 3/2009 Harlev et al.
7,515,954 B2 4/2009 Harlev et al.
7,736,785 B2 6/2010 Oda et al.
7,751,882 B1 7/2010 Helland
7,761,142 B2 7/2010 Ghanem et al.
7,761,150 B2 7/2010 Ghanem et al.
7,907,994 B2 * 3/2011 Stolarski .................. A61B 5/35 600/515
7,930,018 B2 4/2011 Harlev et al.
7,930,020 B2 4/2011 Zhang et al.
8,048,063 B2 11/2011 Aeby et al.
8,150,502 B2 4/2012 Kumar et al.
8,160,682 B2 4/2012 Kumar et al.
8,165,666 B1 4/2012 Briggs et al.
8,165,671 B2 4/2012 Freeman et al.
8,175,702 B2 5/2012 Efimov et al.
8,244,335 B2 8/2012 Kumar et al.
8,521,266 B2 8/2013 Narayan et al.
8,538,503 B2 9/2013 Kumar et al.
8,560,046 B2 10/2013 Kumar et al.
8,594,777 B2 * 11/2013 Briggs ................... A61B 5/287 600/515
8,639,325 B2 1/2014 Efimov et al.
8,647,284 B2 2/2014 Afonso
8,676,303 B2 3/2014 Narayan
8,700,140 B2 4/2014 Narayan et al.
8,838,222 B2 9/2014 Narayan et al.
8,838,223 B2 9/2014 Narayan et al.
8,852,130 B2 10/2014 Govari
8,868,169 B2 10/2014 Narayan et al.
8,911,917 B2 12/2014 Sato et al.
9,050,006 B2 * 6/2015 Narayan .............. A61B 5/7203

(56) References Cited

U.S. PATENT DOCUMENTS 9,055,877 B2 6/2015 Narayan et al.
9,055,878 B2 6/2015 Narayan et al.
9,089,269 B2 7/2015 Narayan et al.
9,107,600 B2 * 8/2015 Narayan ................ G16H 40/67
9,173,670 B2 11/2015 Sepulveda et al.
9,220,427 B2 12/2015 Narayan et al.
9,236,883 B2 1/2016 Guha
9,241,649 B2 1/2016 Kumar et al.
9,241,667 B2 1/2016 Narayan et al.
9,282,910 B2 3/2016 Narayan et al.
9,332,915 B2 5/2016 Narayan et al.
9,392,948 B2 7/2016 Briggs et al.
9,398,883 B2 7/2016 Narayan et al.
9,408,536 B2 8/2016 Narayan et al.
9,451,975 B2 9/2016 Sepulveda et al.
9,474,491 B2 10/2016 Li et al.
9,597,004 B2 3/2017 Hughes et al.
9,642,674 B2 5/2017 Chmiel et al.
9,730,603 B2 8/2017 Laughner et al.
9,808,171 B2 * 11/2017 Balachandran ........ A61B 34/20
9,872,653 B2 1/2018 Li et al.
9,955,887 B2 5/2018 Hughes et al.
10,098,559 B2 10/2018 Hughes et al.
10,123,703 B2 11/2018 Bardy et al.
10,136,828 B2 * 11/2018 Houben ............. A61B 18/1206
10,143,374 B2 12/2018 Ruppersberg
10,201,277 B2 2/2019 Ruppersberg
10,221,551 B2 3/2019 Gray
10,271,754 B2 4/2019 Bahney et al.
10,299,691 B2 5/2019 Hughes et al.
D852,965 S 7/2019 Bahney et al.
10,362,952 B2 7/2019 Basu et al.
10,362,953 B2 7/2019 Basu
10,517,500 B2 12/2019 Kumar et al.
10,772,522 B2 9/2020 Zadig
10,806,343 B2 10/2020 Ruppersberg
10,820,800 B2 11/2020 Ruppersberg
10,888,236 B2 1/2021 Ruppersberg
10,980,418 B2 4/2021 Ruppersberg
11,291,395 B2 4/2022 Ruppersberg
11,389,102 B2 7/2022 Haeusser et al.
2001/0037522 A1 11/2001 Pool et al.
2001/0056245 A1 12/2001 Mlynash et al.
2002/0010392 A1 1/2002 Desai
2002/0016548 A1 2/2002 Stadler et al.
2002/0151808 A1 * 10/2002 Schwartzman ........ A61B 5/341
600/512
2003/0036696 A1 2/2003 Willis et al.
2003/0079278 A1 5/2003 Tash
2003/0236466 A1 12/2003 Tarjan et al.
2004/0073262 A1 4/2004 Lovett
2004/0133113 A1 7/2004 Krishnan
2004/0243011 A1 12/2004 Plaza
2005/0148892 A1 7/2005 Desai
2005/0182336 A1 8/2005 Sippens Groenewegen
2005/0203502 A1 9/2005 Boveja et al.
2006/0084870 A1 4/2006 Kim et al.
2006/0084970 A1 4/2006 Beatty et al.
2006/0093891 A1 5/2006 Issacci et al.
2006/0111700 A1 5/2006 Kunis et al.
2006/0161069 A1 7/2006 Li
2006/0161206 A1 7/2006 Efimov et al.
2007/0055167 A1 3/2007 Bullinga
2007/0073179 A1 * 3/2007 Afonso .................. A61B 5/287
600/523
2007/0208260 A1 9/2007 Afonso
2007/0219454 A1 * 9/2007 Guzzetta ................ A61B 5/349
600/509
2007/0299351 A1 12/2007 Harlev et al.
2008/0009758 A1 1/2008 Voth
2008/0051704 A1 2/2008 Patel et al.
2008/0097539 A1 4/2008 Belalcazar
2008/0109041 A1 5/2008 De Voir
2008/0114258 A1 5/2008 Zhang et al.
2008/0161669 A1 7/2008 Hauck et al.
2008/0193308 A1 8/2008 Korcoban
2008/0245955 A1 10/2008 Tachi et al.
2008/0275367 A1 11/2008 Barbagli et al.
2009/0069704 A1 3/2009 Macadam et al.
2009/0099468 A1 4/2009 Thiagalingam et al.
2009/0112106 A1 4/2009 Zhang
2009/0112110 A1 4/2009 Zhang
2009/0112199 A1 4/2009 Zhang et al.
2009/0171274 A1 7/2009 Harlev et al.
2009/0177071 A1 7/2009 Harlev et al.
2009/0177072 A1 7/2009 Harlev et al.
2009/0177095 A1 7/2009 Aeby et al.
2009/0275828 A1 11/2009 Shachar et al.
2009/0299424 A1 12/2009 Narayan
2010/0000357 A1 1/2010 Gutmann et al.
2010/0030063 A1 2/2010 Lee et al.
2010/0035122 A1 2/2010 Yamamoto et al.
2010/0058519 A1 3/2010 Davenport
2010/0094274 A1 4/2010 Narayan et al.
2010/0129694 A1 5/2010 Sugiura et al.
2010/0204592 A1 8/2010 Hatib et al.
2010/0217143 A1 8/2010 Whittington et al.
2010/0249627 A1 9/2010 Zhang et al.
2010/0280402 A1 11/2010 Dunbar et al.
2010/0298729 A1 11/2010 Zhang et al.
2010/0305456 A1 12/2010 Brainard, II
2011/0087121 A1 4/2011 Zhang et al.
2011/0112425 A1 5/2011 Muhlsteff et al.
2011/0130801 A1 6/2011 Maskara et al.
2011/0196249 A1 8/2011 Staeuber et al.
2011/0213231 A1 9/2011 Hall et al.
2011/0219526 A1 9/2011 Keegan
2011/0251505 A1 10/2011 Narayan et al.
2011/0257547 A1 10/2011 Zhang
2011/0270046 A1 11/2011 Paul et al.
2011/0282227 A1 11/2011 Zhang
2012/0009502 A1 1/2012 Darling et al.
2012/0011643 A1 1/2012 Schultz
2012/0129071 A1 5/2012 Sato et al.
2012/0129073 A1 5/2012 Spencer et al.
2012/0232417 A1 9/2012 Zhang
2012/0233757 A1 9/2012 Slot
2012/0238889 A1 9/2012 Yu et al.
2012/0247519 A1 10/2012 Dondurur et al.
2012/0271135 A1 10/2012 Burke et al.
2012/0283590 A1 * 11/2012 Afonso .................. A61B 5/316
600/523
2012/0321987 A1 12/2012 Goto et al.
2013/0006131 A1 * 1/2013 Narayan ................ A61B 5/283
606/32
2013/0102868 A1 4/2013 Fandrey et al.
2013/0150740 A1 6/2013 Narayan et al.
2013/0150742 A1 6/2013 Briggs et al.
2013/0204142 A1 8/2013 Bertholds et al.
2013/0220032 A1 8/2013 Packirisamy et al.
2013/0226016 A1 8/2013 Narayan et al.
2013/0245476 A1 9/2013 Takizawa et al.
2013/0331718 A1 12/2013 Narayan et al.
2013/0337359 A1 12/2013 Sugiura et al.
2014/0066787 A1 3/2014 Narayan et al.
2014/0073981 A1 3/2014 Narayan et al.
2014/0088395 A1 * 3/2014 Dubois .................. A61B 5/339
600/382
2014/0114204 A1 4/2014 Narayan et al.
2014/0209797 A1 7/2014 Klimovitch
2014/0228696 A1 8/2014 Narayan et al.
2014/0276152 A1 9/2014 Narayan et al.
2014/0343388 A1 * 11/2014 Thakur ................ A61B 5/7246
600/374
2014/0364848 A1 12/2014 Heimbecher et al.
2015/0057522 A1 * 2/2015 Nguyen ................. A61B 5/287
600/374
2015/0065836 A1 * 3/2015 Thakur .................. A61B 5/287
600/374
2015/0073246 A1 * 3/2015 Chmiel .............. A61B 18/1492
600/374
2015/0104729 A1 4/2015 Ishida et al.
2015/0105645 A1 4/2015 Subramaniam et al.
2015/0126840 A1 5/2015 Thakur et al.

(56) References Cited

U.S. PATENT DOCUMENTS

2015/0126993 A1 5/2015 Gelbart et al.
2015/0164349 A1 6/2015 Gopalakrishnan et al.
2015/0208937 A1 7/2015 Bullinga
2015/0216438 A1* 8/2015 Bokan .................... A61B 5/316 600/515
2015/0250424 A1 9/2015 Govari et al.
2015/0254419 A1* 9/2015 Laughner ............. A61B 5/6852 703/11
2015/0273541 A1 10/2015 Kim
2015/0289781 A1 10/2015 Grunwald et al.
2015/0313491 A1* 11/2015 Edwards ................. G16Z 99/00 600/509
2015/0350502 A1 12/2015 Lin
2016/0000357 A1* 1/2016 Harlev ................. A61B 5/7203 600/424
2016/0073960 A1 3/2016 Jung et al.
2016/0184028 A1 6/2016 Warner et al.
2016/0374582 A1 12/2016 Wu et al.
2017/0018205 A1 1/2017 Santhanam et al.
2017/0022694 A1 1/2017 Broten
2017/0027465 A1* 2/2017 Blauer ................. A61B 5/6858
2017/0035497 A1 2/2017 Nagale et al.
2017/0065198 A1* 3/2017 Ruppersberg .......... A61B 5/341
2017/0164858 A1 6/2017 Basu
2017/0178403 A1 6/2017 Krummen et al.
2017/0202471 A1 7/2017 Urman et al.
2017/0202515 A1 7/2017 Zrihem et al.
2017/0202521 A1 7/2017 Urman et al.
2017/0303807 A1 10/2017 Laughner et al.
2018/0342072 A1 11/2018 Raudins
2019/0125186 A1 5/2019 Ruppersberg
2019/0142271 A1 5/2019 Ruppersberg
2019/0284757 A1 9/2019 Chopra et al.
2019/0329302 A1 10/2019 Wu
2019/0357793 A1 11/2019 Ruppersberg
2020/0024839 A1 1/2020 Tapper
2020/0046245 A1 2/2020 Qu et al.
2020/0240127 A1 7/2020 Tash
2020/0245885 A1 8/2020 Haeusser et al.
2020/0345261 A1 11/2020 Haeusser et al.
2021/0000369 A1 1/2021 Luksic et al.
2021/0068694 A1 3/2021 Chou et al.
2021/0259765 A1 8/2021 Narayan
2021/0282693 A1 9/2021 Ruppersberg et al.
2021/0393187 A1 12/2021 Amos et al.
2022/0245885 A1 8/2022 Pags et al.
2022/0345261 A1 10/2022 Ali et al.
2022/0387099 A1 12/2022 Cohen et al.
2024/0033008 A1 2/2024 Govari et al.

FOREIGN PATENT DOCUMENTS

EP 2638852 A1 9/2013
EP 2641557 A1 9/2013
EP 3192445 A1 7/2017
EP 3346914 A1 7/2018
EP 3346915 A1 7/2018
EP 3375365 A2 9/2018
EP 3192438 B1 8/2019
EP 3556284 A3 12/2019
EP 3686899 A1 7/2020
EP 3747356 A1 12/2020
EP 3918998 A1 12/2021
EP 3984457 A1 4/2022
EP 4029449 A1 7/2022
EP 4098198 A2 12/2022
EP 4119054 A1 1/2023
EP 4248859 A1 9/2023
ES 2706537 A1 3/2019
JP 63-270026 A 11/1988
JP 2012-164467 A 8/2012
WO 01/67950 A1 9/2001
WO 2012/092016 A1 7/2012
WO 2012/173697 A1 12/2012
WO 2013/106559 A2 7/2013
WO 2014/007871 A1 1/2014
WO 2014/036439 A2 3/2014
WO 2014/124231 A1 8/2014
WO 2014/168987 A1 10/2014
WO 2015/000870 A1 1/2015
WO 2015/001097 A1 1/2015
WO 2015/066678 A2 5/2015
WO 2015/113770 A1 8/2015
WO 2015/120961 A1 8/2015
WO 2015/130824 A1 9/2015
WO 2016/077786 A1 5/2016
WO 2017/041892 A1 3/2017
WO 2017/042623 A1 3/2017
WO 2017/125114 A1 7/2017
WO 2019/063861 A1 4/2019

OTHER PUBLICATIONS

International Preliminary Report on Patentability received for PCT application No. PCT/EP2016/001513, mailed on Mar. 22, 2018, 12 pages.
International Preliminary Report on Patentability received for PCT application No. PCT/EP2016/001514, mailed on Mar. 22, 2018, 10 pages.
International Preliminary Report on Patentability received for PCT Patent Application No. PCT/EP2016/000087, mailed on Aug. 2, 2018, 9 pages.
International Preliminary Report on Patentability received for PCT Patent Application No. PCT/EP2016/000870, mailed on Dec. 14, 2017, 8 pages.
International Preliminary Report on Patentability received for PCT Patent Application No. PCT/EP2016/001515, mailed on Feb. 16, 2018, 26 pages.
International Preliminary Report on Patentability received for PCT Patent Application No. PCT/IB2016/001273, mailed on Mar. 22, 2018, 7 pages.
International search Report and written opinion received for PCT application No. PCT/EP2016/001513, mailed on Feb. 2, 2017, 16 pages.
International search Report and written opinion received for PCT application No. PCT/EP2016/001514, mailed on Jan. 24, 2017, 14 pages.
International Search Report and Written Opinion received for PCT Patent Application No. PCT/EP2016/000087, mailed on Sep. 14, 2016, 10 pages.
International Search Report and Written Opinion received for PCT Patent Application No. PCT/EP2016/000870, mailed on Aug. 25, 2016, 9 pages.
International Search Report and Written Opinion received for PCT Patent Application No. PCT/EP2016/001515, mailed on Nov. 23, 2016, 14 pages.
International Search Report and Written Opinion received for PCT Patent Application No. PCT/IB2016/001273, mailed on Jan. 10, 2017, 9 pages.
Kalifa, et al., "Mechanisms of Wave Fractionation at Boundaries of High Frequency Excltation in the Posterior Left Atrium of the Isolated Sheep Heart During Atrial Fibrillation," Circulation 2006; 113:626-33.
Kirchhof et al, "2016 ESC guidelines for the management of atrial fibrillation developed in collaboration with EACTS," European Heart Journal, vol. 37, Issue 38 2016.
Laughner et al., "Practical Considerations of Mapping Persistent Atrial Fibrillation With Whole-Chamber Basket Catheters," JACC: Clinical Electrophysiology, vol. 2, Issue 1, Feb. 2016, pp. 55-65. Published by Hindawi in Egypt.
Liu et al, 2018, "Visual tracking in high-dimensional particle filter," PLOS ONE 13 (8): e0201872, Aug. 23, 2018.
Lochmatter et al, "Swis Track—A Flexible Open Source Tracking Software for Multi-Agent Systems," 2008 IEEE/RSJ Int'l Conf. Intell. Robots and Systems, France 2008, pp. 4004-4010.
Mcewan et al, "Efficient computational noise in GLSL," Journal of Graphics Tools, 16(2}:85-94, 2012.

(56) References Cited

OTHER PUBLICATIONS

Miroslav Dura et al , "Toward panoramic in situ mapping of action potential propagation in transgenic hearts to investigate initiation and therapeutic control of arrhythmias," Frontiers in Physiology, vol. 5, Sep. 8, 2014 pp. 1-7.
Murali et al., "Cardiac Ambulatory Monitoring. New Wireless Device Validated Against Conventional Holter Monitoring in a Case Series," Front. Cardiovasc. Med., Nov. 30, 2020, vol. 7, Lausanne, Switzerland.
Oesterlein et al, "Basket-Type Catheters: Diagnostic Pitfalls Caused by Deformation and Limited Coverage," BioMed Research International, vol. 2016 Article ID 5340574, published by Elsevier in The Netherlands.
Office Action received for European Application No. 16703057.6, mailed on Jun. 15, 2020, 4 pages.
Office Action received for European Application No. 16763726.3, mailed on Feb. 19, 2019, 6 pages.
Office Action received for European Application No. 16843733.3, mailed on Jul. 22, 2019, 6 pages.
Office Action received for European Application No. 16843733.3, mailed on Jun. 10, 2025, 4 pages.
Office Action received for European Application No. 16843733.3, mailed on Jun. 26, 2023, 4 pages.
Office Action received for European Application No. 18162169.9, mailed on Aug. 26, 2019 5 pages.
Office Action received for European Application No. 18162169.9, mailed on Jun. 26, 2023, 4 pages.
Office Action received for European Application No. 19219296.1, mailed on Jun. 2, 2023, 10 pages.
Office Action received for European Application No. 20181424.1, mailed on Apr. 23, 2024, 4 pages.
Office Action received for European Application No. 21202891.4, mailed on Oct. 16, 2024, 4 pages.
Office Action received for European Application No. 22176716.3, mailed on Jul. 31, 2023, 9 pages.
Office Action received for European Application No. 22184693.4, mailed on Feb. 3, 2025, 6 pages.
Office Action received for European Application No. 22184693.4, mailed on Nov. 10, 2023, 6 pages.
Office Action received for European Application No. 23164010.3, mailed on Aug. 25, 2025, 8 pages.
PCT Application No. PCT/EP2015/001801, filed on Mar. 16, 2017, by Ruppersberg.
PCT Application No. PCT/EP2015/001803, filed on Mar. 16, 2017, by Ruppersberg.
Potse, "Scalable and Accurate ECG Simulation for Reaction-Diffusion Models of the Human Heart," Apr. 20, 2018, 1-14, vol. 9, Art. 370, Frontiers in Physiology, Switzerland.
Rios-Munoz, "Real-time rotational activity detection in atrial fibrillation," Frontiers in Physiology, Mar. 2018, vol. 9, pp. 1-17, Frontiers Media SA, CH.
Rios-Munoz., "Rotor Detection in Atrial Fibrillation," Doctoral Thesis. Universidad Carios III de Madrid. Jun. 2018 159 pages.
Rodrigo, et al, "Body surface localization of left and right atrial high-frequency rotors in atrial fibrillation patients: A clinical-computational study," Heart Rhythm, Sep. 2014.
Smith et al, "Interactive Computer-Assisted Tracking of Speckle Trajectories in Fluorescence Microscopy: Application to Actin Polymerization and Membrane Fusion," Biophysical Journal. 2011. 101. 1794-804. 10.1016/j.bpj.2011.09.007.
Sohal, et al, "Is Mapping of Complex Fractionated Electrograrns Obsolete?" Arrhythm. Electrophysiol. Rev. Aug. 2015; 4(2): 109-1-15.
Strintzis et al, "Maximum likelihood motion estimation in ultrasound image sequences," in IEEE Signal Processing Letters, vol. 4, No. 6, pp. 156-157, Jun. 1997.
Tinevez et al, "TrackMate: An Open and Extensible Platform for Single-Particle Tracking," Methods. 2016. 115. 10.1016/j.ymeth.2016.09.016.
Vassilis Georgiadis et al, "Multielec: A Matlab Based Application for MEA Data Analysis," PLOS ONE, Jun. 15, 2015, pp. 1-17.
Zhu et al, "Real-Time Motion Capture: An Overview," Complex Intelligent and Software Intensive Systems (CISIS) 2016 10th International Conference on, pp. 522-525, 2016.
"An Iterative Image Registration Technique with an Application to Stereo Vision," Bruce D. Lucas, Takeo Kanade, Proceedings of Imaging Understanding Workshop, pp. 121-130(1).
"Chaste: An Open Source C++ Library for Computational Physiology and Biology," Gary R. Mirams, et al. PLOS Computational Biology, Mar. 14, 2013, vol. 9, Issue3, e1002970.
"Horn-Schunck Optical Flow with a Multi-scale Strategy," Enric Meinhardt-Llopis et al., Image Processing on Line, 3 (2013), pp. 151-172.
"Impact of Rotor Ablation in Nonparoxysmal Atrial Fibrillation Patients," Sanghamitra Mohanty, et al., J. of the American College of Cardiology, vol. 68, No. 3, 2016.
"Interpolation with Splines in Tension: A Green's Function Approach," Paul Wessel and David Bercovici, Mathematical Geology, 77-93, vol. 30, No. 1, 1998.
"Lucas/Kanada Meets Horn/Schunck: Combining Local and Global Optic Flow Methods," Andres Bruhh, Joachim Waickert, Christoph Schnorr, International Journal of Computer Vision.
"Moving Surface Spline Interpolation Based on Green's Function," Xingsheng Deng and Zhong-an Tang, Math, Geosci (2011). 43:663-680.
"Novel Sirategy for Improved Substrate Mapping of the Atria Omnipolar Catheter and Signal Processing Technology Assesses Electrogram Signals Along Physiologic and Anatomic Directions," Deno et al., Circulation; Nov. 10, 2015, vol. 132, Issue Suppl. 3.
"Prospectively Quantifying the Propensity for Atrial Fibrillation: A Mechanistic Formulation," Carrick et al. ; Mar. 13, 2015, PLOS ONE, DOI:10.1371 journal.pone.0118746.
"Segmental Boundary Profile of Myocardial Motion to Localize Cardiac Abnormalities," Slamet Riyadi et al, Proceedings of the World Congress on Engineering 2010, vol. 1.
"SimpleFlow: A Non-Iterative, Sublinear Optical Flow Algorithm," Michael Tao et al. Eurographics 2012, vol. 31 (2012), No. 2.
Atienza et al,, "Mechanisms of Fractionated Electrograms Formation in the Posterior Left Atrium During Paroxysmal, Atrial Fibrillation in Humans," J Am Coll Cardiol. Mar. 1, 2011; 57(9): 1081-1092.
Bellmann, "Velocity characteristics of atrial fibrillation sources determined by electrographic flow mapping before and after catheter ablation," Int'l Journal of Card., Feb. 2019, vol. 286, pp. 56-60, Elsevier, NL.
Bellmann, B., Electrographic Flow Mapping—A New Technology for Identification of Atrial Fibrillation Drivers; Jun. 1, 2017; P239; vol. 19; pp. iiiS4-iii55. Europace; Oxford, UK.
Bellmann, Identification of active atrial fibrillation sources and their discrimination from passive rotors , Clinical Research in Cardiology, 2018, 107: 1021-1032.
Cabral et al, "Imaging vector fields using line integral convolution," Technical report, Lawrence Livermore National Lab., CA (United States), 1993.
Cantwell, C.D., "Techniques for automated local activation time annotation & conduction velocity estimation in cardiac mapping," Com. Bio. Med. 65 (2015) 229-242, Elsevier, NL.
Catmull et al, "A class of local interpolating splines," Computer Aided Geometric Design, 317-326. Elsevier, 1974.
Correa de Sa et al., Electrogram Fracfomation—The Relationship between Spatiotemporal Variation of Tissue Excitation and Electrode Spatial Resolution, Circ Arrhythm, Electrophysiol. Dec. 2011; 4(6}: 909-16.
Correll et al, 2006, "Swis Track: A Tracking Tool for Multi-Unit Robotic and Biological Systems," IEEE International Conference on Intelligent Robots and Systems. 2185-2191.
Decision to grant a European patent received for European Application No. 15736393.8, mailed on Sep. 16, 2021, 2 pages.
Decision to grant received for European Application No. 16703057.6, mailed on Oct. 31, 2024, 2 pages.
Decision to grant received for European Application No. 16763726.3, mailed on Jul. 6, 2023, 2 pages.

(56) References Cited

OTHER PUBLICATIONS

Decision to grant received for European Application No. 21176633.2, mailed on Nov. 17, 2022, 2 pages.
Decision to grant received for European Application No. 22176716.3, mailed on May 3, 2024, 3 pages.
Eugene K. Lee et al., Machine learning plus optical flow a simple and sensitive method to detect cardioactive drugs, Nature, vol. 5, Jul. 3, 2015, pp. 1-12.
European Search Report received for European Application No. 18162169.9, mailed on Jun. 28, 2018, 11 pages.
European Search Report received for European Application No. 19170337.0, mailed on Aug. 27, 2019, 12 pages.
Extended European Search Report received for European Application No. 16843733.3, mailed on Sep. 12, 2018, 8 pages.
Extended European Search Report received for European Application No. 18162169.9, mailed on Nov. 19, 2018, 12 pages.
Extended European Search Report received for European Application No. 19170337.0, mailed on Nov. 27, 2019, 11 pages.
Extended European Search Report received for European Application No. 19219296.1, mailed on Jul. 1, 2020, 10 pages.
Extended European Search Report received for European Application No. 20181424.1, mailed on Nov. 2, 2020, 9 pages.
Extended European Search Report received for European Application No. 21176633.2, mailed on Nov. 5, 2021, 7 pages.
Extended European Search Report received for European Application No. 21202891.4, mailed on Feb. 15, 2022, 7 pages.
Extended European Search Report received for European Application No. 22176716.3, mailed on Nov. 29, 2022, 12 pages.
Extended European Search Report received for European Application No. 22184693.4, mailed on Dec. 9, 2022, 9 pages.
Extended European Search Report received for European Application No. 23164010.3, mailed on Jul. 12, 2023, 9 pages.
Ferrer ET, "Detailed Anatomical and Electrophysiological Models of Human Atria and Torso for the Simulation of Atrial Activation" PLOS One, Nov. 2, 2015.
Gall et al, "Functional Categorization of Objects using Real-time Markerless Motion Capture," IEEE Conf. on Computer Vision and Pattern Recognition (CVPR"11), 1969-1976, 2011.
Golemati et al., "Ultrasound-Image-Based Cardiovascular Tissue Motion Estimation," in IEEE Reviews in Biomedical Engineering, vol. 9, pp. 208-218, 2016.
He et al, "Video Target Tracking Based on Adaptive Kalman Filtering, Communications, Signal Processing, and Systems," CSPS 2019. Lecture Notes, vol. 571, Springer, Singapore.
Horn, et al., "Determining Optical Flow," Artificial Intelligence, vol. 17, pp. 185-204, 1981.
Hummel et al., "Atrial mapping with basket catheters—A Basket case?," JACC: Clinical Electrophysiology, vol. 2 Issue 1, Feb. 2016, pp. 66-68. (Hummel et al., continued) published by Elsevier in The Netherlands.
Intention to Grant received for European Application No. 15736393.8, mailed on May 6, 2021, 6 pages.
Intention to grant received for European Application No. 16703057.6, mailed on Jun. 19, 2024, 6 pages.
Intention to grant received for European Application No. 16763726.3, mailed on Mar. 16, 2023, 6 pages.
Intention to grant received for European Application No. 18162169.9, mailed on Aug. 21, 2025, 6 pages.
Intention to grant received for European Application No. 21176633.2, mailed on Jul. 5, 2022, 6 pages.
Intention to grant received for European Application No. 22176716.3, mailed on Dec. 20, 2023, 6 pages.
Extended European Search Report and Search Opinion received for European Application No. 25204955.6, mailed on Mar. 12, 2026, 7 pages.
Extended European Search Report and Search Opinion received for European Application No. 25225296.0, mailed on Mar. 25, 2026, 8 pages.
Office Action received for European Application No. 20181424.1, mailed on Apr. 4, 2026, 6 pages.

* cited by examiner

SYSTEMS, DEVICES, COMPONENTS AND METHODS FOR DETECTING THE LOCATIONS OF SOURCES OF CARDIAC RHYTHM DISORDERS IN A PATIENT'S HEART

PRIORITY, BENEFITS AND CROSS-REFERENCES TO RELATED APPLICATIONS

This patent application is a continuation application of parent U.S. patent application Ser. No. 17/212,789 filed on Mar. 25, 2021 entitled "Systems, Devices, Components and Methods for Detecting the Locations of Sources of Cardiac Rhythm Disorders in a Patient's Heart" to Dr. Peter Ruppersberg, ("the 789 parent patent application" now U.S. Pat. No. 11,839,445) and claims priority and other benefits therefrom. The '789 parent patent application is hereby incorporated by reference herein, in its entirety, to provide continuity of disclosure.

This patent application also claims priority and other benefits through the 789 parent patent application to the following additional patent applications:

(a) U.S. patent application Ser. No. 16/231,883 filed on Dec. 24, 2018 entitled 'Systems, Devices, Components and Methods for Detecting the Locations of Sources of Cardiac Rhythm Disorders in a Patient's Heart" to Dr. Peter Ruppersberg ("the '883 patent application," now U.S. Pat. No. 10,980,418), and of which the '789 patent application is a continuation;

(b) U.S. patent application Ser. No. 15/548,671 filed on Sep. 7, 2016 entitled "Systems, Devices, Components and Methods for Detecting the Locations of Sources of Cardiac Rhythm Disorders in a Patient's Heart" to Dr. Peter Ruppersberg ("the '671 patent application," now U.S. Pat. No. 10,201,277), of which the '883 parent patent application is a continuation, the '671 patent application also being a 371 of the '001273 patent application listed below;

(c) International Patent Application PCT/IB2016/001273 to Ruppersberg filed on Sep. 7, 2016 entitled "Systems, Device, Components and Methods for Detecting the Locations of Sources of Cardiac Rhythm Disorders in a Patient's Heart (hereafter "the '001273 patent application," and to which priority is also claimed in the present patent application);

(d) International Patent Application PCT/EP2015/001801 to Ruppersberg filed on Sep. 7, 2015 entitled "Elongated Medical Device Suitable for Intravascular Insertion and Method of Making an Elongated Medical Device Suitable for Intravascular Insertion" (hereafter "the '001801 patent application," and to which priority is also claimed in the present patent application), and (e) International Patent Application PCT/EP2015/001803 to Ruppersberg filed on Sep. 7, 2015 entitled "Elongated Medical Device Suitable for Intravascular Insertion and Method of Making an Elongated Medical Device Suitable for Intravascular Insertion" (hereafter the '001803 patent application," and to which priority is also claimed in the present patent application).

The '883, 671, '001273, 001801, and 001803 patent applications are also hereby incorporated by reference herein, each in its respective entirety, to provide continuity of disclosure.

FIELD OF THE INVENTION

Various embodiments described and disclosed herein relate to the field of medicine generally, and more particularly to diagnosing and treating cardiac rhythm disorders in a patient's heart using electrophysiological mapping techniques, as well as in some embodiments using imaging, navigation, cardiac ablation and other types of medical systems, devices, components, and methods. Various embodiments described and disclosed herein also relate to systems, devices, components and methods for discovering with enhanced precision the location(s) of the source(s) of different types of cardiac rhythm disorders and irregularities in a patient's heart, such as, by way of example, active rotors, passive rotors, areas of fibrosis, breakthrough points and focus points.

BACKGROUND

Persistent atrial fibrillation (AF) is assumed to be caused by structural changes in atrial tissue, which can manifest themselves as multiwavelet re-entry and/or stable rotor mechanisms (see, e.g., De Grot M S et al, "Electropathological Substrate of Longstanding Persistent Atrial Fibrillation in Patients with Structural Heart Disease Epicardial Breakthrough," Circulation, 2010, 3: 1674-1 682). Radio frequency (RF) ablation targeting such host drivers of AF is generally accepted as the best therapeutic approach. RF ablation success rates in treating AF cases ae currently limited, however, by a lack of diagnostic tools that are capable of precisely determining the source (or type), and location, of such AF drivers. Better diagnostic tools would help reduce the frequency and extent of cardiac ablation procedures to the minimum amount required to treat AF, and would help balance the benefits of decreased fibrillatory burden against the morbidity of increased lesion load.

One method currently employed to local size AF drivers is the TOPERA® RhythmView® system, which employs a basket catheter having 64 electrodes arranged in an 8×8 pattern from which the system records unipolar electrograms or electrogram signals (ECMs). The RhythmView® algorithm creates a propagation map of the 64 electrodes through a phase analysis of EGM peaks after improving the signal to noise ratio through filtering and subtraction of a simulated compound ECG artifact. The RhythmView® algorithm defects where peak sequences between electrodes show a circular pattern candidate for a re-entry cycle and indicates those locations in a Focal Impulse and Rotor Map (FIRM) using A1 to H8 chess field coordinates for the electrodes. The resolution of the TOPERA system is limited by the spacing of the electrodes and consequently does not show the details of the AF drivers it particular, the TOPERA system cannot show it a circular EGM wavefront is actively generated by a reentry mechanism and is therefore is a driver of AF (i.e., an active rotor), or whether a circular EGM wavefront simply represents turbulence passively generated by an EGM wavefront hitting a barrier (i.e., a passive rotor) in addition, the TOPERA system does not show the direction of AF wavefront propagation, and does not provide the spatial or temporal resolution required b detect singularities associated with the generation of an active rotor.

A recent independent multicenter study ("OASIS, impact of Rotor Ablation in Non-Paroxysmal AF Patients: Results from a Randomized Trial," Sanghamira Mohanty, et al, and Andrea Natale, J Am Col I Cardiol, 2016) reported that the results obtained using TOPERA FIRM technology were inferior to those provided by non-specific ablation of the posterior wall of the left atrium. Moreover, the results suggested Mat FIRM based ablation is not sufficient for therapeutic success without pulmonary vein isolation (PVI) being performed in parallel. Although there are some questions about the methodology of this trial, many experts are convinced that the resolution and interpretability of the TOPERA system need to be improved.

In another approach to the problem, Toronto scientists recently presented a strategy to analyze EGM wave propagation using "Omnipolar Mapping," which seeks to measure beat by beat conduction velocity and direction (see. e.g., "Novel Strategy for Improved Substrate Mapping of the Atria: Omnipolar Catheter and Signal Processing Technology Assesses Electrogram Signals Along Physiologic and Anatomic Directions," D. Curtis Deno et al, and Kumaraswamy Nanthakumar: Circulation. 2015,132A19778). This approach starts with the time derivative of a unipolar EGM as measured by a set of electrodes having known distances to one other. Assuming constant velocity, the velocity and direction representing the best fit for a spatial derivative of the measured EGM are calculated and used to represent an estimate of the E field. According to a communication by Dr. Nenthakumar at the 2016 CardioStim Convention in Nice, France, however, this method remains Incapable of dealing successfully with complex data sets, such as those obtained during an episode of AF.

What is needed are improved means and methods of acquiring and processing intracardiac electrogram signals that reliably and accurately yield the precise locations and sources of cardiac rhythm disorders in a patient's heart. Doing so would enable cardiac ablation procedures to be carried out with greater locational precision, and would result higher rates of success in treating cardiac rhythm disorders such as AF.

Accordingly, it is one objective or the present invention to provide an improved system, especially a medical system, and methods for acquiring and processing intracardiac electrogram signals that reliably and accurately yield the precise locations and sources of cardiac rhythm disorders in a patient's heart.

SUMMARY in one embodiment, there is provided a system for detecting in a patient's heart a location of a source of at least one cardiac rhythm disorder, the system comprising at least one computing device comprising at least one non-transitory computer readable medium configured to store instructions executable by at least one processor to perform a method of determining the source and location of the cardiac rhythm disorder in the patient's heart, the computing device being configured to: a) receive electrogram signals, (b) normalize or adjust amplitudes of the electrogram signals; (c) assign predetermined positions of the electrodes on a mapping electrode assembly to their corresponding electrogram signals; (c) provide or generate a two-dimensional (2 D) spatial map of the electrode positions; (d) for discrete or selected times over which the electrogram signals are being processed, process the amplitude-adjusted electro gram signals to generate a plurality of three-dimensional electrogram surfaces corresponding at least partially to the 2D map, one surface being generated for each such time, and (e) process the plurality of three-dimensional electrogram surfaces through time to generate a velocity vector map corresponding at least partially to the 2D map, the velocity vector map being configured to reveal the location of the source of the at least one cardiac rhythm disorder.

In another embodiment, there is provided a method of detecting a location of a source of at least one cardiac rhythm disorder in a patient's heart, the method comprising normalizing or adjusting the amplitudes of electrogram signals acquired from electrodes, especially configured to be located inside the patient's heart, assigning positions or identifiers for each of the electrodes to corresponding individual electrogram signals, providing or generating a two-dimensional (2 D) spatial map of the electrode positions, for each or selected discrete times over which the electrogram signals re being processed, processing the amplitude-adjusted electrogram signals to generate a plurality of three-dimensional electrogram surfaces corresponding at least partially to the 2D map, one surface being generated for each such time, and processing the plurality of three-dimensional electrogram surfaces through time to generate a velocity vector map corresponding at least partially to the 2D map, the velocity vector map being configured to reveal the location of the source of the at least one cardiac rhythm disorder.

Electrogram signals and processed data may be delivered or communicated to the system for performing the method, e.g., via a data carrier, after they have been acquired by the electrodes and stored for later processing by the system and method according to this invention. Further advantageous embodiments of the system and method are disclosed herein or will become apparent to those skilled in the art after having read and understood the claims, specification and drawings hereof.

BRIEF DESCRIPTION OF THE DRAWINGS

Different aspects of the various embodiments will become apparent from the following specification, drawings and claims in which:

FIG. 1(*b*) shows one embodiment of a computer system 300:

FIG. 5(*b*) shows sensed artifacts in electrogram signals;

FIG. 5(*c*) shows the artifacts of FIG. 5(*b*) superimposed on simulated ECO signals;

FIG. 5(*d*) shows a box plot corresponding to an 8×8 array of 64 electrode signals;

FIG. 5(*e*) shows the data of FIG. 5(*d*) after they have been subjected to an electrode signal normalization, adjustment and filtering process;

FIG. 5(*f*) shows a surface generated from the data shown in FIG. 5(*e*);

FIG. 5(*g*) shows wavefront velocity vectors;

The drawings are not necessarily to scale. Uke numbers refer to like parts or steps throughout the drawings.

DETAILED DESCRIPTIONS OF SOME EMBODIMENTS

Described herein ere various embodiments of systems, devices, components and methods for aiding in the diagnosis end treatment cardiac rhythm disorders in a patient's heart using electrophysiological mapping techniques, as well as imaging, navigation, cardiac ablation and other types of medical systems, devices, components, and methods. Various embodiments described and disclosed herein also relate to systems, devices, components and methods for discovering with enhanced precision the location(s) of the source(s) of different types of cardiac rhythm disorders and irregularities. Such cardiac rhythm disorders and irregularities, include, but are not limited to, arrhythmias, atrial fibrillation (AF or A-fib), atrial tachycardia, atrial flutter, paroxysmal fibrillation, paroxysmal flutter, persistent fibrillation, ventricular fibrillation (V-fib), ventricular tachycardia, atrial tachycardia (A-tach), ventricular tachycardia (V-tech), supraventricular tachycardia (SVT), paroxysmal supraventricular tachycardia (PSVT), Wolff-Parkinson-White syndrome, bradycardia, sinus bradycardia, ectopic atrial bradycardia, junctional bradycardia, heart blocks, atrioventricular block, idioventricular rhythm, areas of fibrosis, breakthrough points, focus points, re-entry points, premature atrial contractions (PACs), premature ventricular contractions (PVCs), and other types of cardiac rhythm disorders and irregularities.

Systems and methods configured to defect in a patient's heart a location of a source of a least one cardiac rhythm disorder are disclosed herein. In the following description, for the purposes of explanation, numerous specific details are set forth in order to provide a thorough understand ng of example embodiments or aspects. It w ill be evident, however, to one skied in the art that an example embodiment may be practiced without necessarily using all of the disclosed specific details.

Figure 1A:
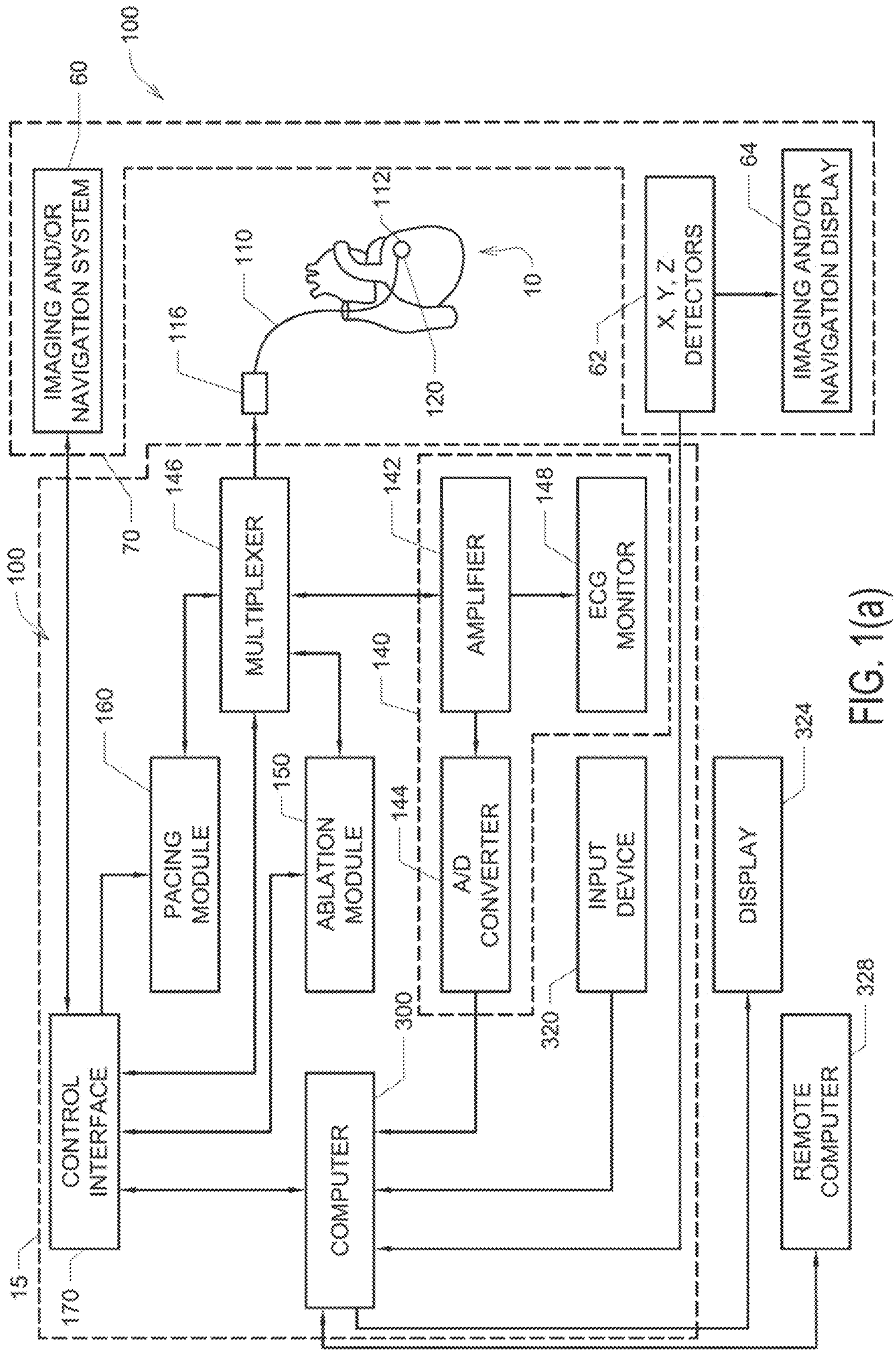
FIG. 1(*a*) shows one embodiment of a combined cardiac electrophysiological mapping (EP), pacing and ablation system 100.
Figure 1B:
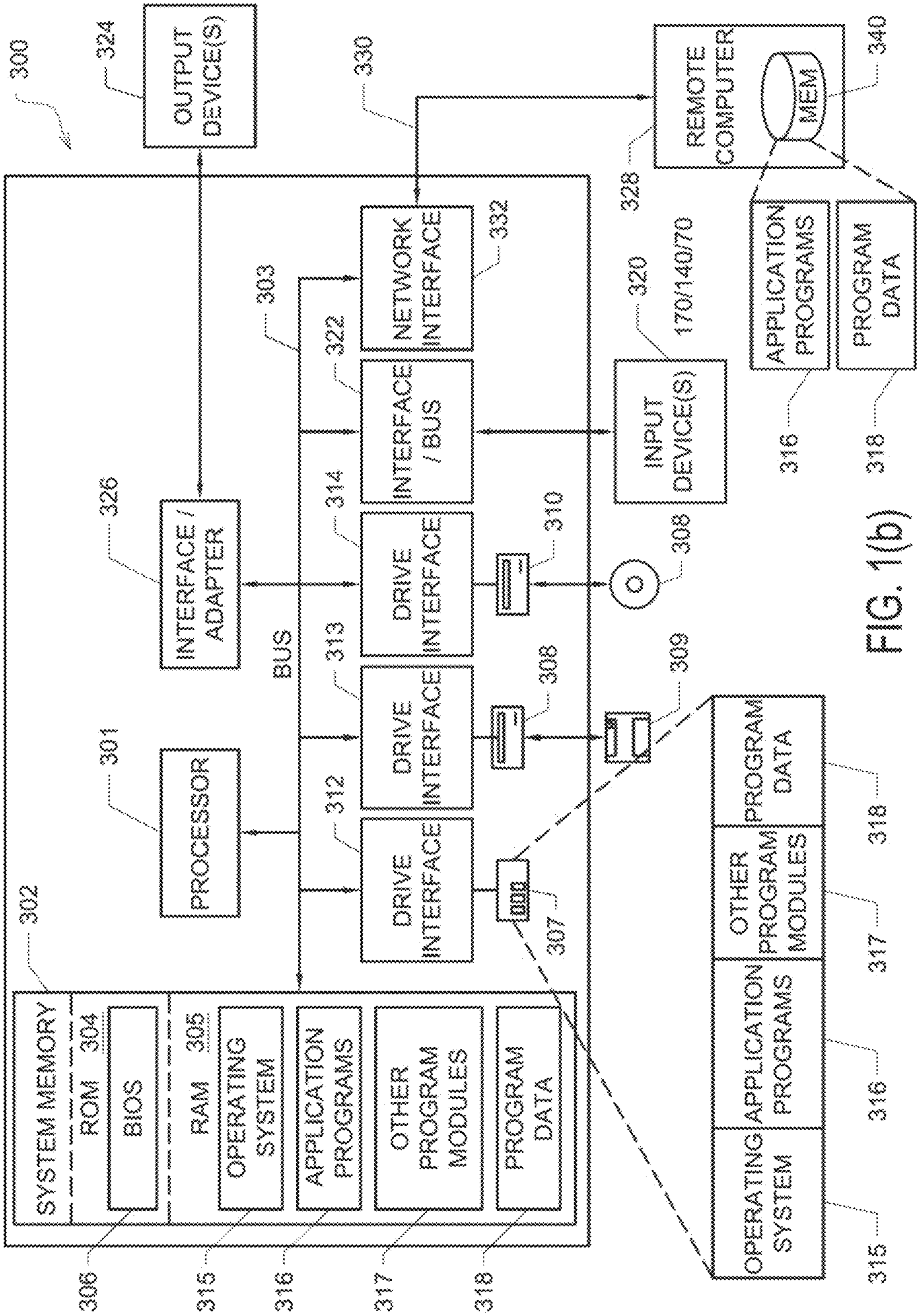

Referring now to FIG. 1(*a*), there is illustrated one embodiment of a combined cardiac electrophysiological (EP) mapping, pacing and ablation system 100. Note that in some embodiments system 100 may not include ablation module 150 and/or pacing module 160. Among other things, the embodiment of system 100 shown in FIG. 1(*a*) is configured to detect and reconstruct cardiac activation information acquired from a patient's heart relating to cardiac rhythm disorders and/or irregularities, and is further configured to detect and discover the location of the source of such cardiac rhythm disorders and/or irregularities with enhanced precision relative to prior art techniques, in some embodiments, system 100 is further con figured to treat the location of the source of the cardiac rhythm disorder or irregularity, for example by ablating the patient's heart at the detected location.

The embodiment of system 100 shown in FIG. 1(*a*) comprises five main functional units: electrophysiological mapping (EP mapping) unit 140 (which is also referred to herein as data acquisition device 140), ablation module 150, pacing module 160, imaging and/or navigation system 70, and computer or computing device 300. In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices.

Computer or computing device 300 may be configured to receive operator inputs from an input device 320 such as a keyboard, mouse and/or control panel. Outputs from computer 300 may be displayed on display or monitor 324 or other output devices (not shown in FIG. 1(*a*)) Computer 300 may also be operably connected to a remote computer or analytic database or server 328. At least each of components, devices, modules and systems 60, 110, 140, 146, 148, 150, 170, 300, 324 and 328 may be operably connected to other components or devices by wireless (e.g., Bluetooth) or wired means. Data may be transferred between components, devices, modules or systems through hardwiring, by wireless means, or by using portable memory devices such as USS memory sticks.

During electrophysiological (EP) mapping procedures, multi-electrode catheter 110 is typical ty introduced percutaneously into the patient's heart 10. Catheter 110 is passed through a blood vessel (not shown), such as a femoral vein or the aorta, and thence into an endocardial site such as the atrium or ventricle of the heart 10.

It is contemplated that other catheters. Including other types of mapping or EP catheters, lasso catheters, pulmonary vein isolation (PVI) ablation catheters (which can operate in conjunction with sensing lasso catheters), ablation catheters, navigation catheters, and other types of EP mapping catheters such as EP monitoring catheters and spiral catheters may also be introduced into the heart, and that additional surface electrodes may be attached to the skin of the patient to record electrocardiograms (ECGs).

When system 100 is operating in an EP mapping mode, multi-electrode catheter 110 functions as a detector of intra-electrocardiac signals, while optional surface electrodes may serve as detectors of surface ECGs. In one embodiment, the analog signals obtained from the intracardiac and/or surface electrodes are routed by multiplexer 146 to data acquisition device 140, which comprises an amplifier 142 and an AD converter (ADC) 144. The amplified or conditioned electrogram signals may be displayed by electrocardiogram (ECC) monitor 148. The analog signals are also digitized via ADC 144 and input into computer 300 for data processing, analysis and graphical display.

In one embodiment, catheter 110 is configured to detect cardiac activation information in the patient's heart 10, and to transmit the detected cardiac activation information to data acquisition device 140, either via a wireless or wired connection. In one embodiment that as not intended to be limiting with respect to the number, arrangement, configuration, or types of electrodes, catheter 110 includes a plurality of 64 electrodes 82, probes and/or sensors A1 through H8 arranged in an 8×8 grid that are included in electrode mapping assembly 120, which is configured for insertion into the patient's heart through the patient's blood vessels and/or veins. Other numbers, arrangements, configurations and types of electrodes 82 in catheter 110 are, however, also contemplated. In most of the various embodiments, at least some electrodes, probes and/or sensors included in catheter 110 are configured to detect cardiac activation or electrical signals, and to generate electrocardiograms or electrogram signals, which are then relayed by electrical conductors from or near the distal end 112 of catheter 110 to proximal and 116 of catheter 110 to data acquisition device 140.

Note that in some embodiments of system 100, multiplexer 146 is not employed for various reasons, such as sufficient electrical conductors being provided in catheter 110 for all electrode channels, or other hardware design considerations, in other embodiments, multiplexer 146 is incorporated into catheter 110 or into data acquisition device 140.

In one embodiment, a medical practitioner or health care professional employs catheter 110 as a roving catheter to locate the site of the location of the source of a cardiac rhythm disorder or irregularity in the endocardium quickly and accurately, without the need for open-chest and open-heart surgery. In one embodiment, this is accomplished by using multi-electrode catheter 110 in combination with real-time or near-real-time data processing and interactive display by computer 300, and optionally in combination with imaging and/or navigation system 70, in one embodiment, multi-electrode catheter 110 deploys at least a two-dimensional array of electrodes against a site of the endocardium al a location that is to be mapped, such as through the use of a Biosense Webster® PENTARAY® EP mapping catheter. The intracardiac or electrogram signals detected by the catheter's electrodes provide data sampling of the electrical activity in the local site spanned by the array of electrodes.

In one embodiment, the electrogram signal data are processed by computer 300 to produce a display showing the locutions(s) of the source(s) of cardiac rhythm disorders and/or irregularities in the patient's heart 10 in real-time or near-real-time, further details of which are provided below. That is, at and between the sampled locations of the patient's endocardium, computer 300 may be configured to compute and display in real-time or near-real-time an estimated, detected and/or determined location(s) of the site(s), source(s) or origin)s) of the cardiac rhythm disorder(s) and/or irregularity(s) with in the patient's heart 10. This permits a medical practitioner to move interactively and quickly the electrodes 82 of catheter 110 to, wards the location of the source of the cardiac rhythm disorder or irregularity.

In some embodiments of system 100, one or more electrodes, sensors or probes detect cardiac activation from the surface of the patient's body as surface ECGs, or remotely without contacting the patient's body (e.g., using magnetocardiograms). In another example, some electrodes, sensors or probes may derive cardiac activation Information from echocardiograms. In various embodiments of system 100, external or surface electrodes, sensors end/or probes can be used separately or in different combinations, and further may also be used in combination with intracardiac electrodes, sensors and/or probes inserted within the patient's heart 10. Many different permutations and combinations of the various components of system 100 are contemplated having, for example, reduced, additional or different numbers of electrical sensing and other types of electrodes, sensors and/or transducers.

Continuing to refer to FIG. 1(*a*), EP mapping system or data acquisition device 140 is configured to condition the analog electrogram signals delivered by catheter 110 from electrodes 82 A1 through H8 in amplifier 142. Conditioning of the analog electrogram signals received by amplifier 142 may include, but ii not limited to, low-pas filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

As discussed above, in some embodiments, multiplexer 146 is separate from catheter 110 and data acquisition device 140, and in other embodiments multiplexer 146 is combined in catheter 110 or data acquisition device 140.

In some embodiments, the rate at which individual electrogram and/or ECG signals are sampled and acquired by system 100 can range between about 0.25 milliseconds and about 8 miniseconds, and may be about 0.5 milliseconds, about 1 millisecond, about 2 milliseconds or about 4 miniseconds. Other sample rates are also contemplated. While in some embodiments system 100 is configured to provide unipolar signals, in other embodiments system 100 is configured to provide bipolar signals.

In one embodiment, system 100 can include a BARD® LABSYSTEM™ PRO EP Recording System, which is a computer and software driven data acquisition and analysis tool designed to facilitate the gathering, display, analysis, pacing, mapping, and storage of intracardiac EP data. Also in one embodiment, data acquisition device 140 can include a BARD® CLEARSIGN™ amplifier, which as configured to amplify and condition electrocardiographic signals of biologic origin and pressure transducer input, and transmit such information to a host computer (e.g., computer 300 or another computer).

As shown in FIG. 1(*a*), and as described above, in some embodiments system 100 includes ablation module 150, which may be configured to deliver RF ablation energy through catheter 110 and corresponding ablation electrodes disposed near distal end 112 thereof, and/or to deliver Rr ablation energy through a different catheter (not shown in FIG. 1(*a*)). Suitable ablation systems and devices include, but are not limited to, cryogenic ablation devices and/or systems, radiofrequency ablation devices and/or systems, ultrasound ablation devices and/or systems, high-intensity focused ultrasound (HIFU) devices end/or systems, chemical ablation devices and/or systems, and laser ablation devices and/or systems.

When system 100 is operating in an optional ablation mode, multi-electrode catheter 110 fitted with ablation electrodes, or a separate ablation catheter, is energized by ablation module 150 under the control of computer 300, control interface 170, and/or another control device or module. For example, an operator may Issue a command to ablation module 150 through input device 320 to computer 300. In one embodiment, computer 300 or another device controls ablation module 150 through control interface 170. Control of ablation module 150 can initiate the delivery of a programmed series of electrical energy pulses to the endocardium via catheter 110 (or a separate ablation catheter, not shown in FIG. 1(*a*)). One embodiment of an oblation method and device is closed in U.S. Pat. No. 5,383,917 to Desai et al., the entirety of which is hereby incorporated by reference herein.

In an alternative embodiment, ablation module 150 is not controlled by computer 300, and is operated manually directly under operator control. Similarly, pacing module 160 may also be operated manually directly under operator control. The connections of the various components of system 100 to catheter 110, to auxillary catheters, or to surface electrodes may also be switched manually or using multiplexer 146 or another device or module.

When system 100 is operating in an optional pacing mode, multi-electrode catheter 110 is energized by pacing module 160 operating under the control of computer 300 or another control device or module. For example, an operator may issue a command through input device 320 such that computer 300 controls pacing module 160 through control interface 170, and multiplexer 146 initiates the delivery of a programmed series of electrical simulating pulses to the endocardium via the catheter 110 or another auxiliary catheter (not shown in FIG. 1(*a*)). One embodiment of a pacing module is disclosed in M. E. Josephson et al., in "VENTRICULAR ENDOCARDIAL PACING li, The Role of Pace Mapping to Localize Origin of Ventricular Tachycardia", The American Journal of Cardiology, vol. 50, November 1982.

Computing device or computer 300 it appropriately configured and programmed to receive or access the electrogram signals provided by data acquisition device 140. Computer 300 is further configured to analyze or process such electrogram signals in accordance with the methods, functions and logic disclosed and described herein so as to permit reconstruction of cardiac activation information from the electrogram signals. This, in turn, makes it possible to locate with ae least some reasonable degree of precision the location of the source of a heart rhythm disorder or irregularity. Once such a location has been discovered, the source may be eliminated or treated by means that include, but are not limited to, cardiac ablation.

In one embodiment, and as shown in FIG. 1(*a*), system 100 also comprises a physical imaging and/or navigation system 70. Physical imaging and/or navigation device 60 included in system 70 may be, by way of example, a 2- or 3-axis fluoroscope system, an ultrasonic system, a magnetic resonance imaging (MRI) system, a computed tomography (CT) imaging system, and/or an electrical impedance tomography EIT) system. Operation of system 70 be controlled by computer 300 via control interface 170, or by other control means incorporated into or operably connected to imaging or navigation system 70. In one embodiment, computer 300 or another computer triggers physical imaging or navigation system 60 to take "snapshot" pictures of the heart 10 of a patient (body not shown). A picture image is detected by a detector 32 along each axis of imaging, and can include a silhouette of the heart as well as a display of the inserted catheter 110 and its electrodes 82 A1-H8 (more about which is said below), which is displayed on imaging or navigation display 64. Digitized image or navigation data may be provided to computer 300 for processing and integration into computer graphics that are subsequently displayed on monitor or display 64 and/or 324.

In one embodiment, system 100 further comprises or operates in conjunction with catheter or electrode position transmitting and/or receiving coils or antennas located at or near the distal end of an EP mapping catheter 110, or that of an ablation or navigation catheter 110, which are configured to transmit electromagnetic signals for ultra-body navigational and positional purposes.

In one embodiment, imaging or navigation system 70 is used to help identify and determine the precise two- or three-dimensional positions of the various electrodes included in catheter 110 with in patterns head 10, and is configured to provide electrode position data to computer 300. Electrodes, position markers, and/or radio-opaque markers can be located on various portions of catheter 110, mapping electrode assembly 120 and/or distal end 112, or can be configured to act as fiducial markers or imaging or navigation system 70.

Medical navigation systems suitable for use in the various embodiments described and dis closed herein include, but are not limited to, image-based navigation systems, model-based navigation systems, optical navigation systems, electromagnetic navigation system (e.g., BIOSENSE® WEBSTER™ CARTO™ system), and impedance-based navigation systems (e.g., the St. Jude® ENSITE™ VELOCITY™ cardiac mapping system), and systems that combine attributes from different types of imaging AND navigation systems and devices to provide navigation with in the human body (e.g., the MEDTRONIC® STEALTHSTATION® system).

In view of the structural and functional descriptions provided herein, those skilled in the an will appreciate that portions of the described devices and methods may be configured as methods, data processing systems, or computer algorithms. Accordingly, these portions of the devices and methods described herein may take the form of a hardware embodiment, a software embodiment, or an embodiment combining software and hardware, such as shown and described with respect to computer system 300 illustrated in FIG. 1(*b*). Furthermore, portions of the devices and methods described herein, may be a computer algorithm stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, systems, and computer algorithm products. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be snored in a computer-readable memory that can direct computer 300 or other programmable data processing apparatus to function in a particular manner, such that the instructions stored an the computer-readable memory result in an article of manufacture including instructions which implement the function specified in an individual block, plural ty of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in an individual block, plurality of blocks, or block diagram.

In this regard. FIG. 1(*b*) illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image date, and/or transform sensor or electrode data and image data associated with the analysis of cardiac electrical activity and the carrying out of the combined electrophysiological mapping and analysis of the patient's heart 10 and ablation therapy delivered thereto.

Computer system 300 can be implemented on one or more general purpose computer systems or networked computer systems, embedded computer systems, routers, switches, server devices, client devices, various intermediate devices/nodes or standalone computer systems. Additionally, computer system 300 or portions thereof may be implemented on various mobile devices such as, for example, a personal digital assistant (PDA), a laptop computer and the like, provided the mobile device includes sufficient processing capabilities to perform the required functionality.

In one embodiment, computer system 300 includes processing unit 301 (which may comprise a CPU, controller, microcontroller, processor, microprocessor or any other suitable processing device), system memory 302, and system bus 303 that operably connects various system components, including the system memory, to processing unit 301. Multiple processors and other multi-processor architectures also can be used to form processing unit 301. System bus 303 can comprise any of several types of suitable bus architectures, including a memory bus or memory controller, a peripheral bus, or a local bus. System memory 302 can include read only memory (ROM) 304 and random access memory (RAM) 305. A basic input/output system (BIOS) 306 can be stored in ROM 304 and contain basic routines configured to transfer information and/or data among the various elements within computer system 300.

Computer system 300 can include a hard disk drive 303, a magnetic disk drive 308 (e.g., to read from or write to removable disk 309), or an optical disk drive 310 (e.g., for reading CDROM disk 311 or to read from or write to other optical media). Hard disk drive 303, magnetic disk drive 308, and optical disk drive 310 are connected to system bus 303 by a hard disk drive interface 312, a magnetic disk drive interface 313, and an optical drive interface 314, respectively. The drives and their associated computer-readable media are configured to provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the devices and methods described and disclosed herein.

A number of program modules may be stored in drives and RAM 303, including operating system 316, one or more application programs 316, other program modules 313, and program data 318. The application programs and program date can include functions and methods programmed to acquire, process and display electrical data from one or more sensors, such as shown and described herein. The application programs and program data can include functions and methods programmed and configured to process data acquired from a patient, e.g. for assessing heart function, such as shown and described herein with respect to FIGS. 1-10(*f*).

A health care provider or other user may enter commands and information into computer system 300 through one or more input devices 320, such as a pointing device (e.g., a mouse, a touch screen, etc.), a keyboard, a microphone, a Joystick, a game pad, a scanner, and the like. For example, the user can employ input device 320 to edit or modify the date being input into a data processing algorithm (e.g., only data corresponding to certain time intervals). These and other input devices 320 may be connected to processing unit 301 through a corresponding input device interface or port 322 that is operably coupled to the system bus, but may be connected by other interfaces or ports, such as a parallel port, a serial port, or a universal serial bus (USB). One or more output devices 324 (e.g., display, a monitor, a printer, a projector, or other type of display device) may also be operably connected to system bus 303 via interface 326, such as through a video adapter.

Computer system 300 may operate in a networked environment employing logical connections to one or more remote computers, such as remote computer 328. Remote computer 328 may be a workstation, a computer system, a router, or a network node, and may include connections to many or all the elements described relative to computer system 300. The logical connections, schematically indicated at 330, can include a local area network (LAN) and/or a wide area network (WAN).

When used in a LAN networking environment, computer system 300 can be connected to a local network through a network interface or adapter 332. When used in a WAN networking environment, computer system 300 may include a modem, or may be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

Figure 2:
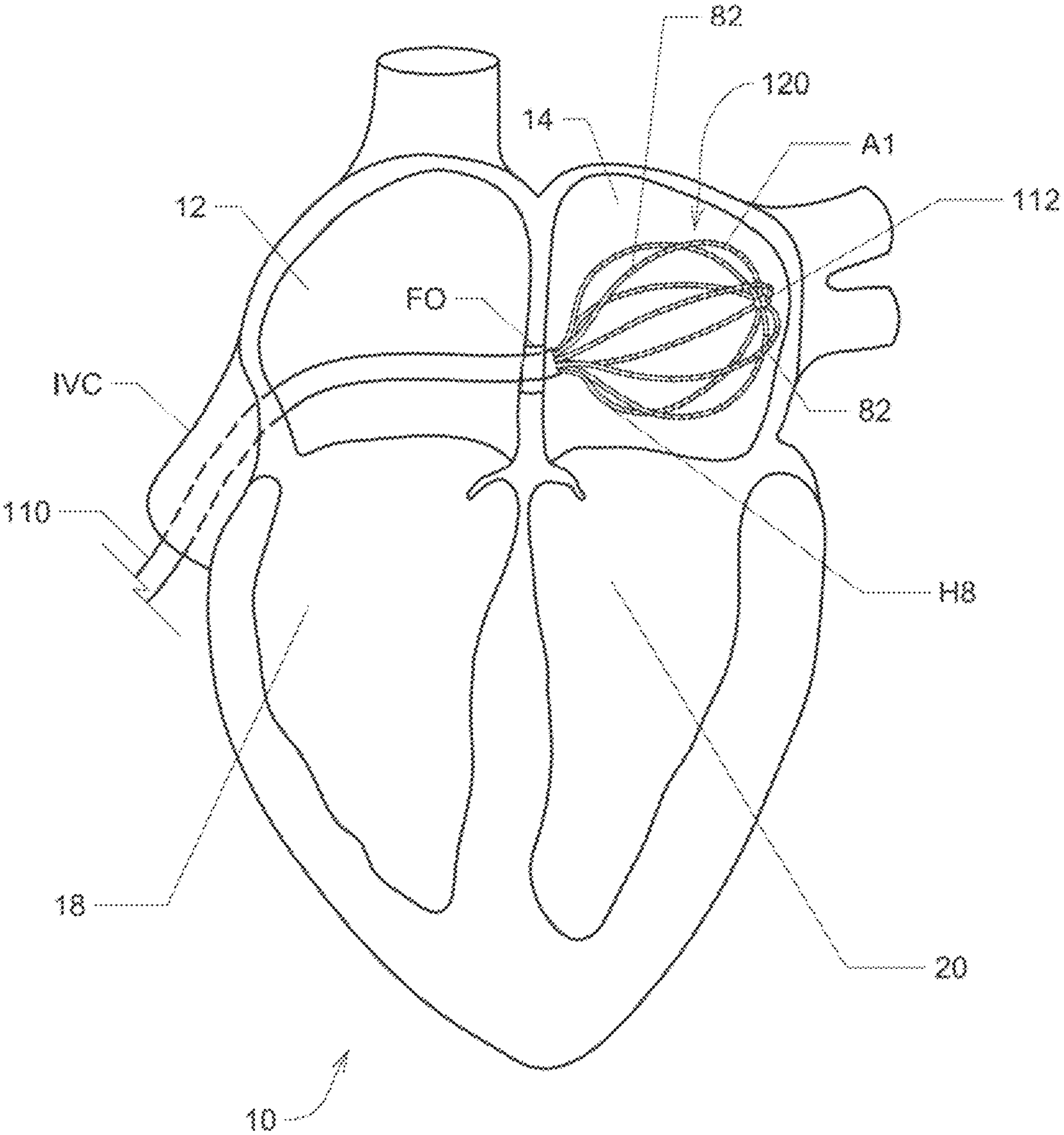
FIG. 2 shows an illustrative view of one embodiment of a distal portion of catheter 110 inside a patient's left atrium 14.
Figure 3:
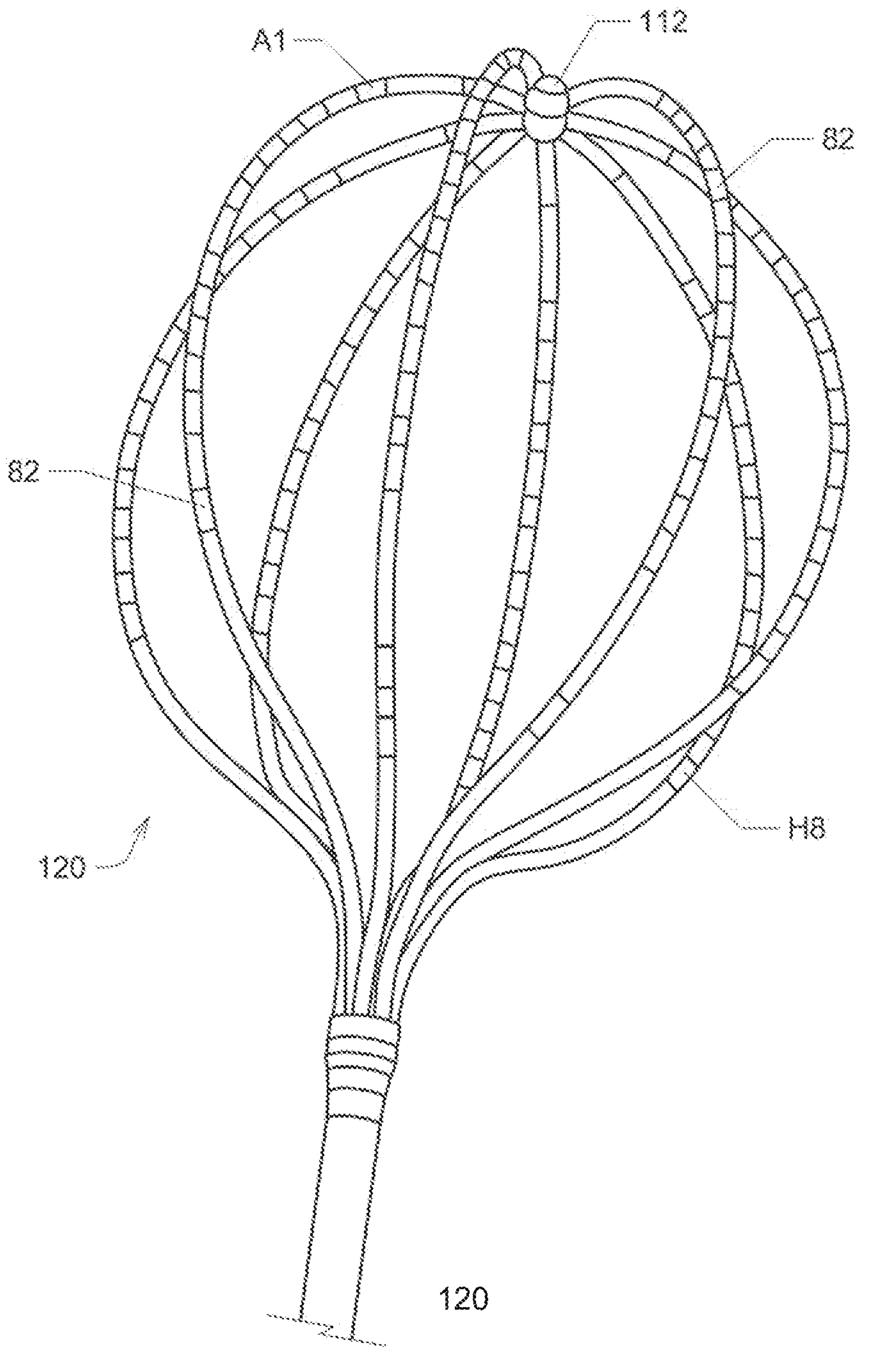
FIG. 3 shows an illustrative embodiment of a mapping electrode assembly 120 of catheter 110 of FIG. 2.

Referring now to FIG. 2, there is shown an illustrative view of one embodiment of a distal portion of catheter 110 inside a patient's left atrium 14. As shown in FIG. 2, heart 10 includes right atrium 12, left atrium 14, right ventricle 18, and left ventricle 20. Mapping electrode assembly 120 is shown in an expended or open state inside left atrium 13 after it has been inserted through the patient's inferior vena cava and foramen ovalen ("IVC" and "FW" in FIG. 2), and is configured to obtain electrogram signals from left atrium 12 via an 8×8 array of electrodes 82 A1 through H8. Mapping electrode assembly and catheter 110 may also be positioned with the patient's right atrium 12, left ventricle 18 and right ventricle 20, FIG. 3 shows an illustrative embodiment of a mapping electrode assembly 120, which in FIG. 3 forms a distal portion of a Boston Scientific a CONSTELLATION® full contact mapping catheter. The CONSTELLATION EP catheter permits full-contact mapping of a patient's heart chamber, and may also be employed to facilitate the assessment of entrainment, conduction velocity studies, and refractory period in a patient's heart 10. Mapping electrode assembly 120 shown in FIG. 3 permits the simultaneous acquisition of longitudinal and circumferential signals for more accurate 3-D mapping, and features a flexible basket design that conforms to atrial anatomy and aids aid in accurate placement. Sixty-four electrodes 82 A1 through H8 can provide comprehensive, real-time 3-D information over a single heartbeat.

Figure 4:
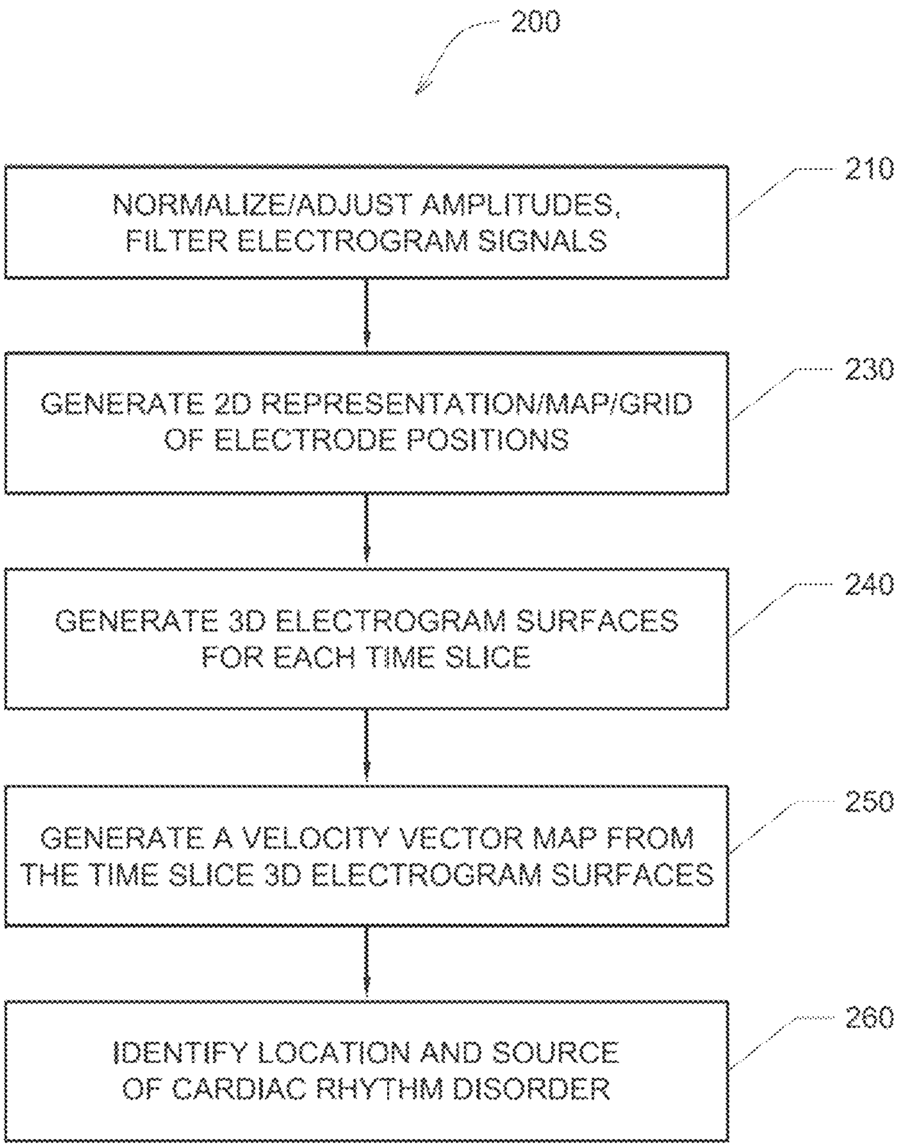
FIG. 4 shows one embodiment of an algorithm or method 200 of detecting a location of a source of at least one cardiac rhythm disorder in a patient's heart.
Figure 5A:
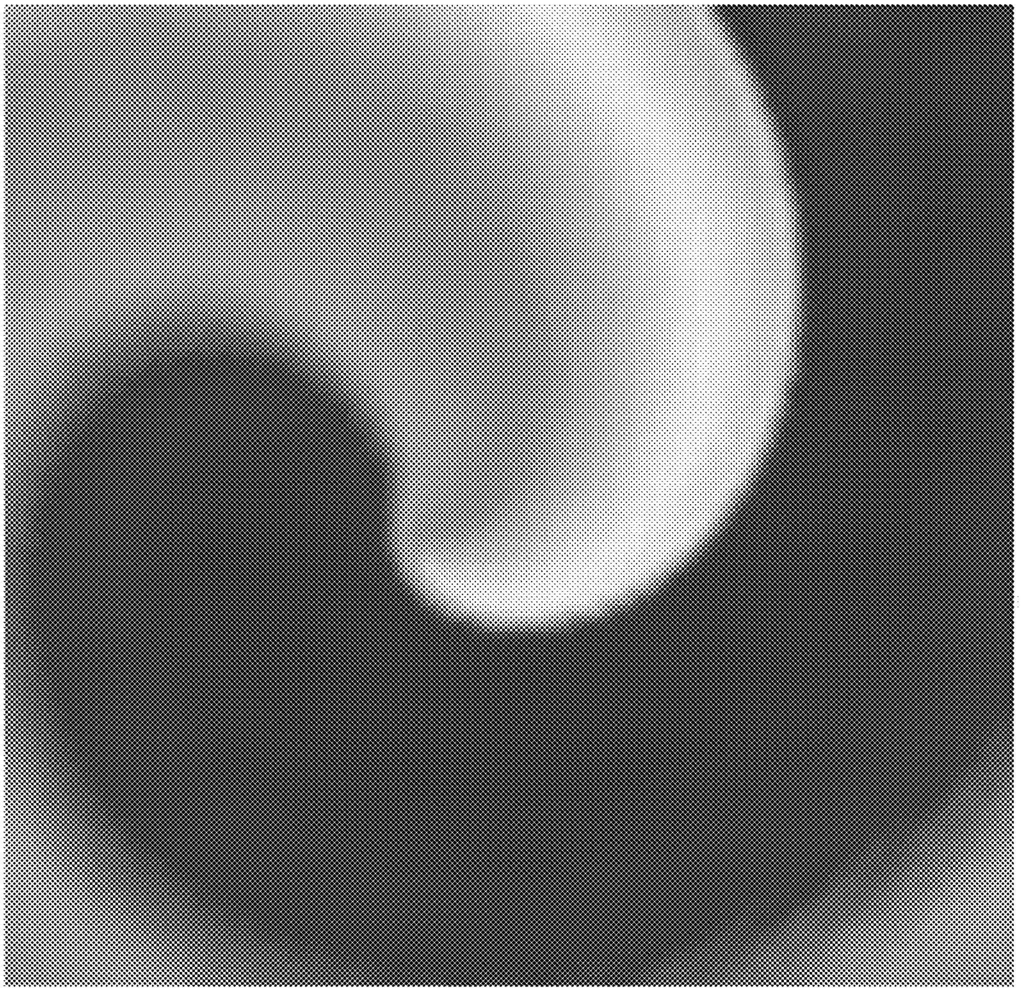
FIG. 5(*a*) shows a simple rotor model.
Figure 5B:
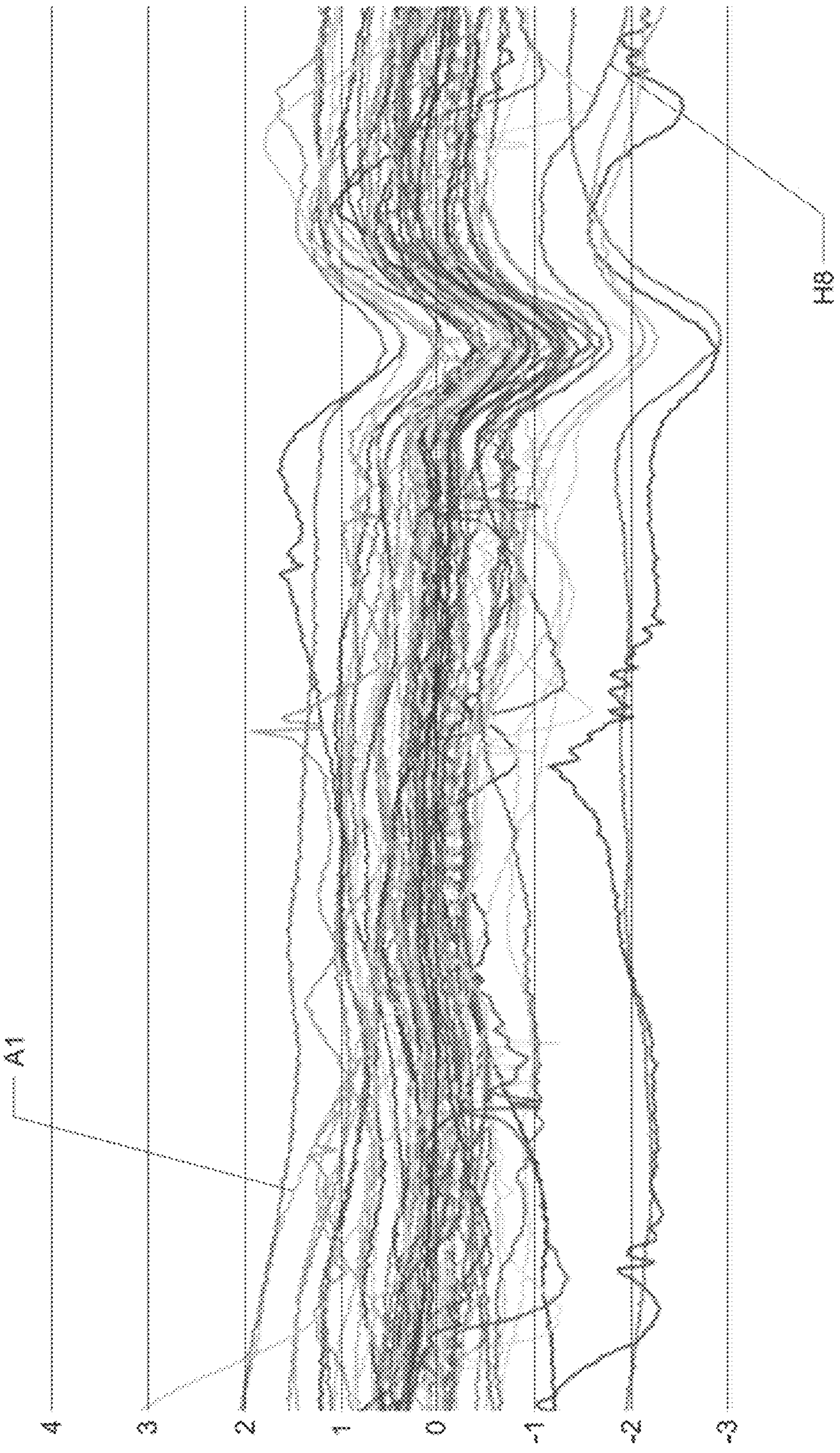
Figure 5C:
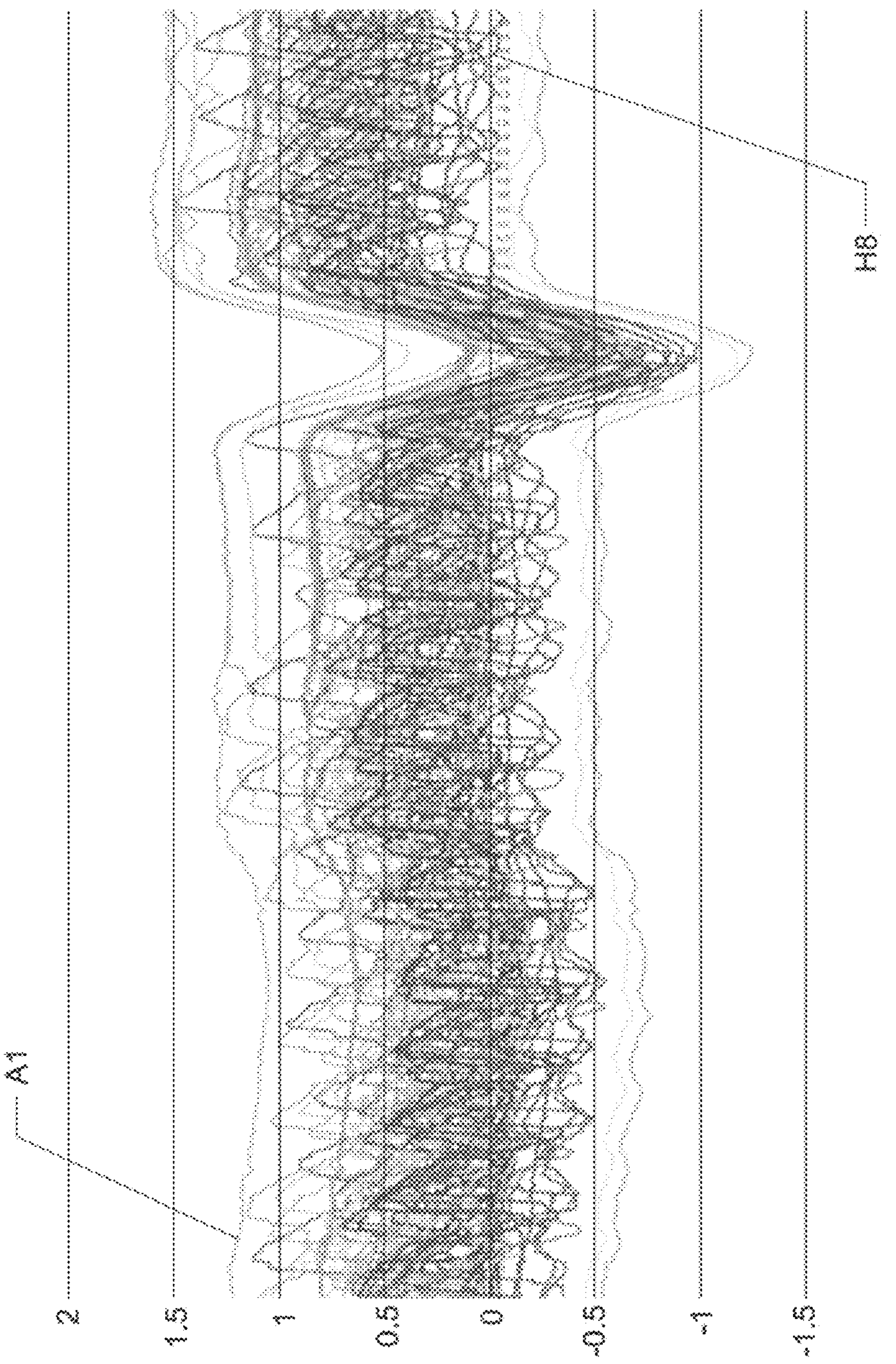
Figure 5D:
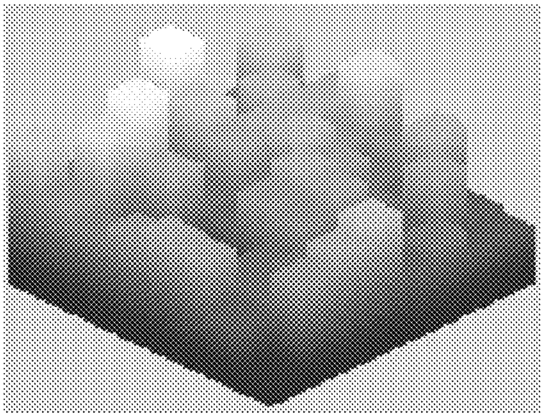
Figure 5E:
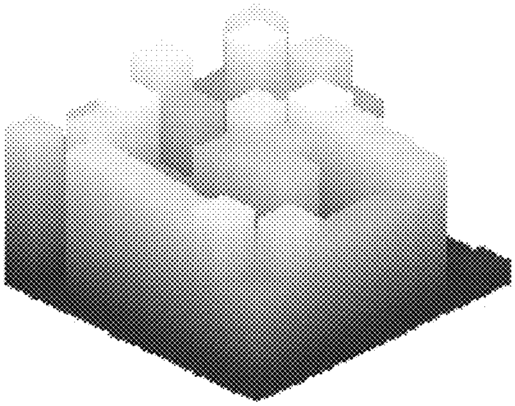
Figure 5F:
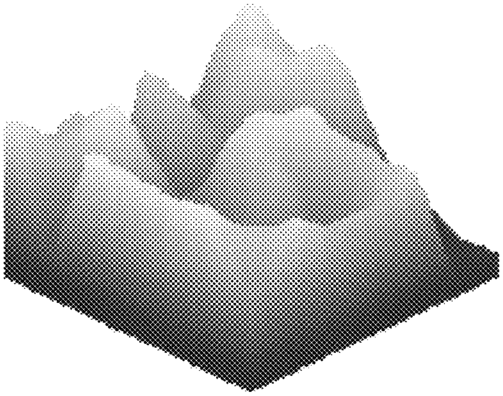
Figure 5G:
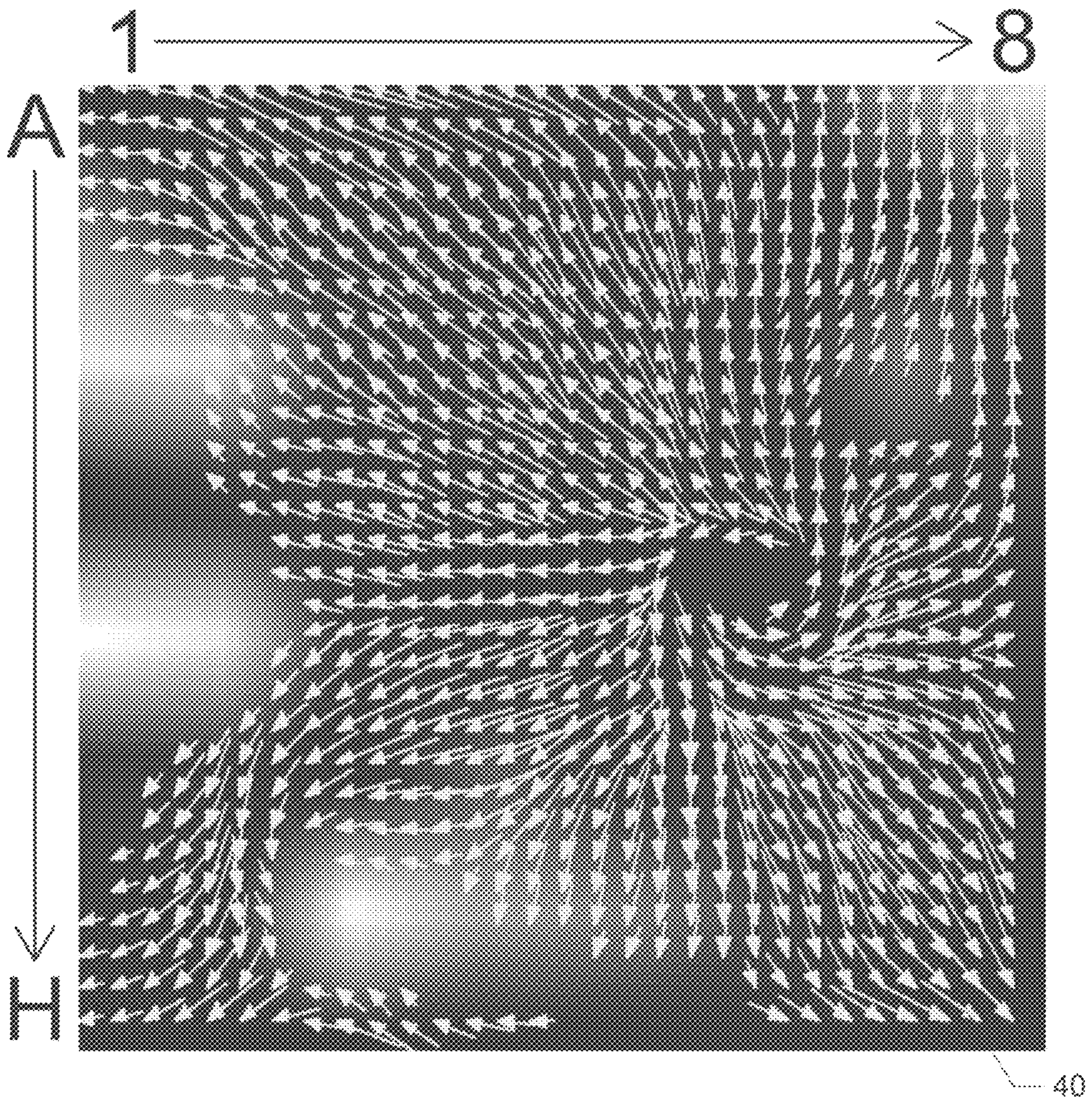

FIG. 4 shows one embodiment of a method 200 of detecting a location of a source of at least one cardiac rhythm disorder in a patient's heart. At step 210, the amplitudes of electrogram signals acquired from electrodes 82 located inside a patient's heart, e.g., electrodes 82 included in a mapping electrode assembly 120, are normalized and/or adjusted. At step 230, positions A1 through H8 corresponding to each of the electrodes 82 of mapping electrode assembly 120 are assigned to the individual electrogram signals that have been acquired. At step 230, a two-dimensional (2D) spatial map of electrode positions A1 through H8 is generated or provided, in some embodiments, a three-dimensional (30) spatial map of electrode positions A1 through H8 is generated or provided. (As discussed above, fewer or more than 64 electrodes 82 may be used to measure electrogram signals and/or surface ECCs, and electrode arrays other than 8×8 or rectangular grids are contemplated in the various embodiments.) For discrete or selected times over which the electrogram signals are being analyzed and processed, at step 240 the amplitude-adjusted electrogram signals are processed across the 2D (or 3D) map to generate a plurality of three-dimensional electrogram surfaces (which according to one embodiment may be smoothed electrogram surfaces) one surface being generated for each such discrete time. At step 250, the plurality of three-dimensional electrogram surfaces that have been generated across the 2D (or 3D) map through time are processed to generate a velocity vector map. The velocity vector map is configured to reveal the location of the source of the at least one cardiac rhythm disorder. In a subsequent optional step (not shown in FIG. 4), method 200 further comprises ablating patient's heart 10 at the location of the source of the cardiac rhythm disorder indicated by the velocity vector map.

Algorithm 200 outlined in FIG. 4 presents one embodiment of a method of processing electrogram signals provided by one or more mapping catheters so as to transform time domain waveform information into space domain information, and then calculate velocity vector maps that correspond to normalized space potential profile movements for each point in space. For reasons that are explained below, algorithm 200 has the advantages that it is robust against artifacts and provides a virtual resolution that is higher than the actual electrode density employed to acquire the EP mapping date through the use of a fitting algorithm that determines the most likely mean spatial velocity map derived from hundreds of individual samples of amplitude patterns recorded by the mapping electrodes.

As described above, in step 210 of FIG. 4 the amplitudes of electrogram signals acquired from electrodes located inside the patient's heart are normalized or otherwise adjusted. In step 240, the amplitude-adjusted electrogram signals are processed across a 2D or 3D map to generate a plurality of three-dimensional electrogram surfaces, one surface being generated for each such discrete time. In one embodiment, the resulting individual time-slice surfaces can be strung together sequentially to provide a time-varying depiction of electrical activation occurring over the portion of the patient's heart that has been monitored. According to embodiments that have been discovered to be particularly efficacious in the field of intracardiac EP monitoring and data processing and analysis, at least portions of the electrogram surfaces are found to correspond to estimated wave shapes, and are generated using Green's function, which in some embodiments, and by way of non-limiting example, may be combined with two- or three dimensional bi-harmonic spline interpolation functions to generate such surfaces.

In one embodiment, electrogram signal date acquired from the patient's heart 10 are not equidistantly sampled. For example, in one such embodiment, electrogram signal data acquired from the patient's heart 10 are not equidistantly sampled by mapping electrode assembly 120, and instead are assigned their respective chessboard locations At through H8 as approximations of electrode locations in a cylindrical 20 projection of a grid representative of the interior surface of me patient's head that is being mapped. In many applications, it has been discovered that such approximations of electrode locations yield perfectly useable and accurate results when steps 230 through 250 are carried out after steps 210 and 230.

In another embodiment, when superimposing the acquired electrogram signal data onto a 2D or 3D map or grid in step 230, the electrogram signal data may be associated with their actual or more accurately estimated positions in the 2 D projection of the grid using positional data provided by, for example, imaging or navigation system 70. Resampling of electrogram signals on the grid may also be carried out. Gridding may also be carried out such as by convolution-type filtering, Kriging, and using splines. Most gridding techniques operate on an equidistant grid and solve the equations governing the gridding process with either fin its difference or finite element implementations.

One approach that has been discovered to work particularity well with electrogram signal data is to determine the Green's function associated with each electrogram value assigned to a given chessboard location, and then construct the solution as a sum of contributions from each data point, weighted by the Green's function evaluated for each point of separation. Biharmonic spline interpolation, which can be used in conjunction with Green's function, has also been discovered to work especially well in the context of processing and analyzing electrogram signal data. In some embodiments, undesirable oscillations between data points are removed by interpolation with splines in tension based on Green's function. A Green's function technique for Interpolation and surface fitting and generation of electrogram signal data has been found to be superior to conventional finite-difference methods because, among other things, the model can be evaluated at arbitrary x,y locations rather than only on a rectangular grid. This is a vary important advantage of using Green's function in step 240, because precise evenly-spaced-apart grid locations, resampling of electrogram signals, and finite-difference gridding calculations am not required to generate accurate representations of electrogram surfaces in step.

In one embodiment. Green's function G(x; x') is employed in step 240 for a chosen spine and geometry to interpolate data at regular or arbitrary output locations. Mathematically, the solution is w(x)=sum {c(i) G(x'; x(i))}, for i=1, n, and a number of data points {x(i), w(i)}. Once the n coefficients c(i) have been calculated, the sum may be evaluated at any output point x. A selection is made between min mum curvature, regularized, or continuous curvature splines in tension for either 1-D, 2-D, or 3-D Cartesian coordinates or spherical surface coordinates. After removing a linear or planar trend (i.e., in Cartesian geometries) or mean values (i.e., spherical surfaces) and normalizing residuals, a least-squares matrix solution for spline coefficients c(i) may be determined by solving the n by n linear system w(j)=sum-over-i {c(i) G(x(j); x(i))}, for j=1, n; this solution yields an exact interpolation of the supplied data points. For further details regarding the algorithms and mathematics underlying Green's function, see: (1) "Moving Surface Spine Interpolation Based on Green's Function," Xingsheng Deng and Zhong-an Tang. Math. Geosci (2011). 43:663-680 ("the Deng paper"), and (2) "Interpolation with Splines in Tension: A Green's Function Approach." Paul Wesel and David Bercovici, Mathematical Geology, 77-03, Vol, 30, No. 1, 1998 ("the Wessel paper"). The respective entireties of the Deng and Wessel papers are hereby incorporated by reference herein.

Still further details regarding the use of Green's function in interpolating and generating surfaces may be found in: Interpolation by regularized spline with tension: I. Theory and Implementation, Mitasova, H., and L. Mitas, 1993, Math. Geol., 25, 641-6: Parker. R. I., 1994. Geophysical Inverse Theory, 386 pp., Princeton Univ. Press, Princeton, N.J.; Sandwell, D. T., 1987, Biharmonic spline interpolation of Geos-3 and Seasat altimeter data, Geophys. Res Lett., 14, 139-142: Wessel, P., and J. M. Besker, 2008, Interpolation using a generalized Green's function for a spherical surface spline in tension, Geophys. J. Int. 174, 21-28, and Wessel, P., 2000, A general-purpose Green's function interpolator, Computers & Geosciences, 35, 1247-1254, Moving Surface Spline Interpolation Based on Green's Function, Xingsheng Deng. Zhong-an Tang. Mathematical Geosciences, August 2011, Volume 43, Issue 6, pp 663-680.

Note, however, that a number of different surface smoothing, surface fitting, surface estimation and/or surface/data interpolation processing techniques may be employed in step 240 of FIG. 4, which are not limited to Green's function, and which include, but are not limited to, inverse distance weighted methods of interpolation, triangulation with linear interpolation, bilinear surface interpolation methods, bivariate surface interpolation methods, cubic convolution interpolation methods. Kriging interpolation methods. Natural Neighbor or "area-stealing" interpolation methods, spline interpolation techniques (including bi-harmonic spline fitting techniques and "spline with barriers" surface interpolation methods), global polynomial interpolation methods, moving least squares interpolation methods, polynomial least square fitting interpolation methods, simple weighted-average operator interpolation methods, multi, quadric biharmonic function interpolation methods, and artificial neural network interpolation methods. See, for example: "A brief description of natural neighbor interpolation (Chapter 2)," in V. Barnett. Interpreting Multivariate Data. Chichester: John Wiley, pp. 21-36.), and "Surfaces generated by Moving Least Squares Methods," P. Lancaster et al., Mathematics of Computation, Vol. 37. No. 155 Qul., 1901), 141-158).

As described above, in step 250 of FIG. 4, the plurality of three-dimensional electrogram surfaces may be Processed across the 2D or 3D map through time to generate a velocity vector map, the velocity vector map being configured to reveal the location of the source of the at least one cardiac rhythm disorder. According to embodiments that have been discovered to be particularly efficacious in the field of intracardiac EP monitoring and subsequent data processing and analysis, at least portions of the velocity vector map are generated using one or more optical flow analysis and estimation techniques and methods. Such optical flow analysis techniques may include one or more of Horn-Schunck, Buxton-Buston, Black-Jepson, phase correlation, block-based, discrete optimization, Lucas-Kanade, and differential methods of estimating optical How. From among these various optical flow estimation and analysis techniques and methods, however, the Horn-Schunck method has so far been discovered to provide superior results in the context of processing and analyzing cardiac electrogram signals, for reasons that are discussed in further detail below.

Two papers describe the Horn-Schunck method particularly well: (1) "SimpleFlow: A Non-Iterative, Sublinear Optical Flow Algorithm," Michael Tao et al., Eurographics 2012 Vol. 31 (2012), No. 2 ("the Tao paper"), and (2) "Horn-Schunck Optical Flow with a Multi-Scale Strategy," Enric Meinhardt-Llopis et al., Image Processing On Line, 3 (2013), pp. 151-172 ("the Meinhardt-Llopis paper"). The respective entireties of the Tao and Meinhardt-Llopis papers are hereby incorporated by reference herein.

In "Determining Optical Flow," by B. K. P. Horn and a. C. Schunck, Artificial Intelligence, Vol. 17. pp. 185-204, 1981 the entirety of which is also hereby incorporated by reference herein, a method for finding an optical flow pattern is described which assumes that the apparent velocity of a brightness pattern varies smoothly throughout most of an image. The Horn-Schunck algorithm assumes smoothness in flow over most or all of an image. Thus, the Horn-Schunck algorithm attempts to minimize distortions in flow and prefers solutions which exhibit smoothness. The Horn-Schunck method of estimating optical flow is a global method which introduces a global constraint of smoothness to solve the aperture problem of optical flow.

A description of some aspects of conventional application of the Horn-Schunck method is set forth in U.S. Pat. No. 6,480,615 to Sim et al., entitled "Motion estimation with s; a sequence of data frames using optical flow with adaptive gradients," the entirety of which 6 also hereby incorporated by reference herein. As described by Sun et al., the Horn-Schunck computation is based on the observation that flow velocity has two components, and that a rate of change of image brightness requires only one constraint. Smoothness of flow is introduced as a second constraint to solve for optical low. The smoothness constraint presumes there are no spatial discontinuities. As a result, Horn and Schunck excluded situations where objects in an image occlude or block one another. This is because at object boundaries of an occlusion in an image, discontinuities in reflectance appear.

In conventional optical flow analysis, image brightness is considered a pixel (x, y) in an image plane at time I to be represented as a function I(x, y, t). Based on initial assumptions that the intensity structures of local time-varying image regions are approximately constant under motion for at least a short duration, the brightness of a particular point in the image is constant, so that dl/dt=0. Based on the chain rule of differentiation, an optical flow constraint equation (I) can be represented as follows:

$$Ix(x, y, t) \cdot u + I\,y(x, y, t) \cdot v + It(x, y, t) = 0,$$

where

Ix×3l(x, y, t)/9x=horizontal spatial gradient of the image intensity;

Iy=5l(x, y, t)/dy=vertical spatial gradient or the image intensity;

It=dl(x, y, t)/3t=temporal image gradient of the image intensity;

u=dx/dt=horizontal image velocity (or displacement); and v=dy/dt=vertical image velocity (or displacement).

The above optical flow equation is a linear equation having two unknowns, {i.e., u and v}. The component of motion in the direction of the brightness gradient is known to be lt/(tx2*ly2)V2. However, one cannot determine the component of movement in the direction of the isobrightness contours at right angles to the brightness gradient. As a consequence, the optical flow velocity (u,v) cannot be computed locally without introducing additional constraints. Horn and Schunck therefore introduce a smoothness constraint. They argue that if every point of the brightness pattern can move independently, then there is little hope of recovering the velocities. However, if opaque objects of finite size are undergoing rigid motion or deformation, neighboring points on the objects should have similar velocities. Correspondingly, the velocity field of the brightness patterns in the image will very smoothly almost everywhere.

Advantages of the Horn-Schunck algorithm include that it yields a high density of flow vectors, i.e., the flow information missing in inner parts of homogeneous objects is flied in from the motion boundaries. On the negative side, the Horn-Schunck algorithm can be sensitive to noise.

The foregoing discussion regarding how the Horn-Schunck optical flow technique typically focuses on conventional applications, where the brightness or intensity of an object changes over time (which is where the term "optical Row" is derived from). Here, the brightness or intensity of an object is not the issue at hand, instead, the amplitudes of electrogram signals, and how they change shape and propagate in time and space over a patient's heart, are sought to be determined. One underlying objective of method or algorithm 200 is to produce a vector velocity map, which se a representation of electrographically flow (and not optical flow) within e.g. a patient's heart. Instead of looking for differences or changes in optical brightness or intensity, changes in the velocity, direction and shape of electrical signals (i.e., changes in electrographical flow) across a patient's heart are determined. That is, algorithm 200 does not process optical measurement data corresponding to intensity or brightness, but processes electrical measurement data corresponding to amplitude, potential shape, and/or voltage. One of the reasons why algorithm 200 works so well in detecting the locations of the sources of cardiac rhythm disorders and irregularities is that ion channels in a patient's heart produce action potential voltages that are relatively constant (except in areas of fibrosis. As described above, the Horn-Schunck method assumes "brightness constancy" as one of its key constraints. The normalized/amplitude-adjusted electrogram signals provided by step 210 help satisfy this key constraint of the Horn-Schunck method so that this method may be applied successful ty in step 250.

In addition, because of the stability imparted to electrographical flow solutions determined using the Horn-Schunck method, artifacts and noise are generally low in velocity vector maps generated in step 2350. In fact, it is believed that the Horn-Schunck method may generally be applied with greater success to electrographical flow data than to optical data because of the unique nature of action potential signals in the human heart, and the manner in which electrogram signals are processed and conditioned before an optical flow analysis is performed on them as described and disclosed herein.

Algorithm 200 described and disclosed herein also does not employ spatial derivatives of electrical potentials (as is done by Deno et al, and Kumaraswamy Nanthakumar using "omnipolar" signals) or time derivatives of electrogram signals (as is done in the TOPERA system). Time derivatives of signals are known to increase noise. Algorithm 200 has as its key inputs the potentials of electrogram signals (not their derivatives). As a result, algorithm 200 is notably free from the effects of spurious noise and artifacts introduced by time-derivative data processing techniques, including in step 250.

In another embodiment, the velocity vector map of step 250 is generated using the Lucas-Kanade optical flow algorithm, which is a differential method for optical flow estimation developed by Bruce D. Lucas and Takeo Kanade, it assumes that the flow is essentially constant in a local neighbourhood of a pixel under consideration, and solves the basic optical now equations for all the pixels in that neighborhood using least squares criteria. By combining information from several nearby pixels, the Lucas-Kanade method can often resolve the inherent ambiguity of the optical flow equation. It is also less sensitive to image noise than point-wise methods. On the other hand, since it is a purely local method, k can not provide now information in the interior of uniform regions of the image. See "An Iterative image Registration Technique with an Application to Stereo Vision," Bruce D. Lucase, Takeo Kanade. Proceedings of imaging Understanding Workshop, pp. 121-130 (1981), the entirety of which is hereby incorporated by reference herein.

In yet another embodiment, various aspects of the Horn-Schunck and Lucas-Kanade algorithms are combined to yield an optical low algorithm that exhibits the local methods inherent in Lucas-Kanade techniques end the global methods inherent in the Horn-Schunck approach and its extensions. Often local methods am more robust under noise, while global techniques yield dense flow fields. See, for example. "Lucas-Kanade Meets Horn/Schunck: Combining Local and Global Optic Flow Methods," Andres Bruhn, Joachim Weickert, Christoph Schnor, International Journal of Computer Vision, February 2005, Volume 61, issue 3, pp 211-231, the entirety of which is hereby incorporated by reference herein.

Various embodiments of algorithm 200 feature several advantages with respect to prior at systems and methods that generate intracardiac images and attempt to detect the locations of cardiac rhythm disorders or irregularities. A key underlying assumption of signal processing techniques that employ Hilbert Transform. Discrete Fourier Transforms (DFTs) or Fast Fourier Transforms (FFTs) is that the signal to be transformed is periodic. As is well known in the field of digital signal processing, this underlying basic assumption is frequently incorrect, and can lead to problems such as spectral leakage. Contrariwise, in some embodiments of algorithm 200, an underlying assumption is that the electrical activity in a patient's heart is based upon ion channel activation, which is a stochastic and non-periodic process, and so strictly periodic behaviour is not assumed or required in subsequent data processing and manipulation steps.

Indeed, none of steps 210, 230, 240, or 250 of method or algorithm 200 absolutely requires the use of Hilbert or Fourier transforms to process data. Instead, in some embodiments each of these steps can be carried out in the time domain without the need for frequency domain or quadrature conversion. For example, in step 210 the amplitudes of the various traces or electrograms can be normalized or adjusted in the time domain according to a selected standard deviation. In another example, rotors detected by algorithm 200 are not assumed to be singularities in a phase map (as is assumed in techniques based upon frequency domain or Hilbert transform signal processing). This key difference also explains why the rotational direction of a rotor can be revealed or detected accurately by algorithm 200 (and not at all, or very unsatisfactory, using the frequency domain or Hilbert transforms of other methods employed to detect rotors). Note that in some embodiments, however, Hilbert, DFT and/or FFT signal processing components may be or are Included in the data processing low of algorithm 200 (e.g., DSP filtering, deconvolution, etc.)

Referring now to FIG. 5(*a*), there Is shown a simple rotor model. This model was used to generate simulated ECG signals sensed by an 8×8 array of virtual electrodes. The simple rotor model shown in FIG. 5(*a*) is from "Chaste: An Open Source C++ Library for Computational Physiology and Biology," Gary R. Mirans, et al. PLOS Computational Biology, Mar. 14, 2013, Vol. 0, Issue 3, e1002970, the entirety of which is hereby incorporated by reference herein.

FIG. 5(*b*) shows artifacts in electrogram signals derived from actual patient data, where 400 msec, traces were recorded using a 64-electrode basket catheter located in the left atrium of a patient suffering from atrial fibrillation. As shown in FIG. 5(*b*), the sensed artifacts in the electrogram signals Include DC offsets of several millivolts that shift with ire, a common farfield ventricular depolarization superimposed on the local potentials sensed by individual electrodes, and noise. Moreover, the amplitudes of the various sensed electrogram signals shown in FIG. 5(*b*) will be seen to vary considerably. These amplitude variations result at least in part on from varying degrees to which individual electrodes touch, or are physically coupled to, the patient's endocardial surface. Electrogram signals corresponding to electrodes in loose, poor or no contact with a patient's endocardium may be an order of magnitude smaller than those where electrodes are well coupled to the endocardial surface.

FIG. 5(*c*) shows the artifacts of FIG. 5(*b*) superimposed on the simulated ECC signals generated from the rotor model of FIG. 5(*a*), FIG. 5(*d*) shows a box plot corresponding to the 8×8 array of 64 electrode signals shown in FIG. 5(*a*) at a selected common time for all traces. Because of the artifacts from FIG. 5(*b*) introduced into the electrogram signals of FIG. 5(*c*), the box plot of FIG. 5(*d*) appears quite irregular and chaotic, and the original spiral shape of the underlying rotor of FIG. 5(*a*) is not discernable to the eye.

The data shown in FIG. 5(*c*) were used to perform an analysis in accordance with algorithm 200, which was carried out in three main steps: (1) normalization/adjustment/filtering of electrogram signals (step 210); (2) generating three-dimensional smoothed electrogram surfaces for discrete times or time slices from the normalized/adjusted/filtered electrogram signals (step 240) generated in the first main step 210, and (3) generating a velocity vector map based on the smoothed electrogram surfaces (step 250) generated in the second main step 240.

Described now is one embodiment and illustrative example of the first main step of the algorithm 200 (normalization/adjustment/filtering of electrogram signals). Referring now to FIG. 5(*e*), there are shown the data of FIG. 5(*d*) after they have been subjected to one embodiment of an electrode signal normalization, adjustment and filtering process. After normalization and filtering, the simple rotor structure shown in FIG. 5(*a*) becomes visible in FIG. 5(*e*). Uniform electrode signal amplitude minima and maxima were first calculated and then applied to individual electrogram signals to generate individual amplitude equalized electrogram signals. Unwanted artifacts such as ventricular depolarization signals were removed from the individual equalized electrogram signals by first averaging all electrogram signals to generate a common electrogram artifact signal, which was then subtracted from each of the equalized individual electrogram signals. The resulting equalized artifact-compensated electrogram signals were then high-pass filtered between 5 and 20 Hz to remove DC offsets from the electrogram signals such that the resulting filtered electrogram signals were approximately zeroed around the X (time) axis. These results are shown in FIG. 5(*e*).

Next, a sliding time window ranging between about 0.1 seconds and about to 1 second in length was applied to each filtered electrogram signal to generate individual amplitude-adjusted electrogram signals. (in some embodiments, the length of the sliding time window corresponds to, or is less then, the slowest repetition frequency expected to be present.) The resulting sliding-window amplitude-adjusted electrogram signals were then stored for later use to generate image backgrounds in velocity vector maps, where they could be used to show low amplitude areas indicative of valve defects/artifacts, loose electrode contact, and/or areas of fibrosis in the patient's myocardium. In the sliding-window amplitude-adjusted electrogram signals, the respective minima and maxima of each position of the sliding time window were used to normalize the amplitude values of all signals between zero and one (or 0 and 255 on an 8-bit integer numeric scale). Because the maximum and minimum values occurred at different time points for electrodes placed in different locations, this process yielded spatial information regarding action potential wave patterns for each sampled time point (more about which is said below).

Now I describe one embodiment and illustrative example of the second main step of the algorithm 200 (generating three-dimensional electrogram surfaces for discrete times or time slices, or estimation of spatial wave shapes). The second step of algorithm 200 takes the spatial distributions of all electrodes 82 and their normalized voltage values at discrete times (e.g., the data represented by the box plot corresponding to selected discrete dimes with in the selected time window over which electrogram signals were acquired and measured) and estimates or generates from such data or box plots corresponding to given discrete times respective continuous voltage surfaces (or action potential waveform estimates) in space. Because the electrode pattern density is limited, and depending on the method that is used to generate the estimated voltage surfaces, the estimated surfaces typically deviate to some extent from "true" surfaces. Such deviations are usually relatively small in magnitude, however, since the spatial size of the action potential wave given by its velocity [e.g., 0.5 to 1 m/sec.) times the action potential duration (e.g., 0.1 to 0.2 sec.) is much larger (e.g., 0.05 m) than the electrode spacing (e.g., about 1 mm to about 10 mm), and thus spatial aliasing generally does not occur. The electrode grid provided by catheter 110 thus permits relatively good estimates of action potential wave shapes or wavefronts in the form of smoothed electrogram surfaces to be obtained as they propagate across the myocardium. On the other hand, because of the fast sampling rate (which can, for example, range between about 0.25 milliseconds and about 8 milliseconds, and which in some embodiments is nominally about 1 millisecond), changes in the spatial shape or expression of the action potential wavefront from one sample to the next are typically relatively small (e.g., about 1 mm) compared to the electrode distances (which in some embodiments nominally range between about 2 mm and about 7 mm). Thus, algorithm 200 is capable of detecting spatial changes in action potential wavefronts or wave shapes using time domain information (i.e. small amplitude changes between lime samples) to estimate changes in the spatial domain (where relatively small shifts in action potentials occur at given electrode measurement locations).

One embodiment of a method for estimating action potential wavefronts or wave shapes employs an 8×8 rectangular electrode grid (e.g., TOPERA®-like) model, which operates in two principal steps. First, each electrode/electrogram signal value at a discrete moment in time defines the height of its respective box in the 'chess field' box plots shown in FIGS. 5(*d*) and 5(*e*). Second, a smoothed electrogram surface is generated for each box plot (or discrete slice of time) by calculating for each horizontal x-y point (typically on a 300×300 grid) an average of neighboring z-values (or electrical potentials) in the box plot. In 3D models that take assumed or actual electrode positions and spacing into account (using, e.g., information from a navigation or imaging system), smoothed electrogram surfaces are generated using 2D biharmonic spline interpolation techniques and Green's function. Using the foregoing simple averaging approach, the smoothed electrogram surface of FIG. 5(*f*) was generated from the data shown in FIG. 5(*e*). As shown in FIG. 5(*f*), a spatial wave shape estimate of a rotor appears prominently in the forward center portion of the resulting smoothed surface, which tracks closely the original spiral wave shown in FIG. 5(*a*).

S Described now is one embodiment and illustrative example of the third main step of algorithm 200 (generating a velocity vector map based on the electrogram surfaces). The third main step of algorithm 200 uses the action potential wave shape estimates or electrogram surfaces generated at discrete times or time splices provided by the second main step to calculate a velocity vector map. For each sample interval a spatial wave shape or smoothed surface is calculated according to the second main step described above, since the wave shapes differ only by a small delta between individual samples, and minimum and maximum values are normalized, shin vectors can be calculated at a spatial resolution that is higher than the spatial resolution of the electrodes 82 (e.g., 30×30 samples). Since individual shifts between samples may differ according to random error, a velocity vector lit can be generated using 40 to 100 samples, where an average of observed shift vectors of the action potential wave shape care calculated. If the angle of a rowing wavefront is shifted by a few degrees per sample, the vector arrows 40 will exhibit a circular pattern and in fact can resolve circles that are much smaller than inter-electrode distances, in one embodiment, the third main step of the algorithm employs a vector pattern equation that best fits the observed movement of the evaluated spatial element or waveform. In one embodiment that has been discovered to provide excellent results, and as described above, the velocity vector map is calculated using the Horn-Schunck optical ow method described above. That is, in one embodiment the Horn. Schunck optical flow method is used in the third main step of algorithm 200 to estimate the velocity and direction of wavefronts or wave shapes between sampled times. Velocities of 40 to 100 samples are typically averaged to yield the most stable results.

FIG. 5(*g*) shows the resulting wavefront velocity vectors indicated by arrows 40) calculated from a series of 60 averaged time slices of smoothed surfaces samples corresponding to the data shown in FIG. 5(*t*. An active rotor is distinctly visible in the right-hand central portion of FIG. 5(*g*), where arrows 40 are flowing tightly in a counterclockwise direction. In FIG. 5(*g*), action potential wavefronts are seen to be moving outwardly away from the detected active rotor (as would be expected in the case of an active rotor)).

Figure 6A:
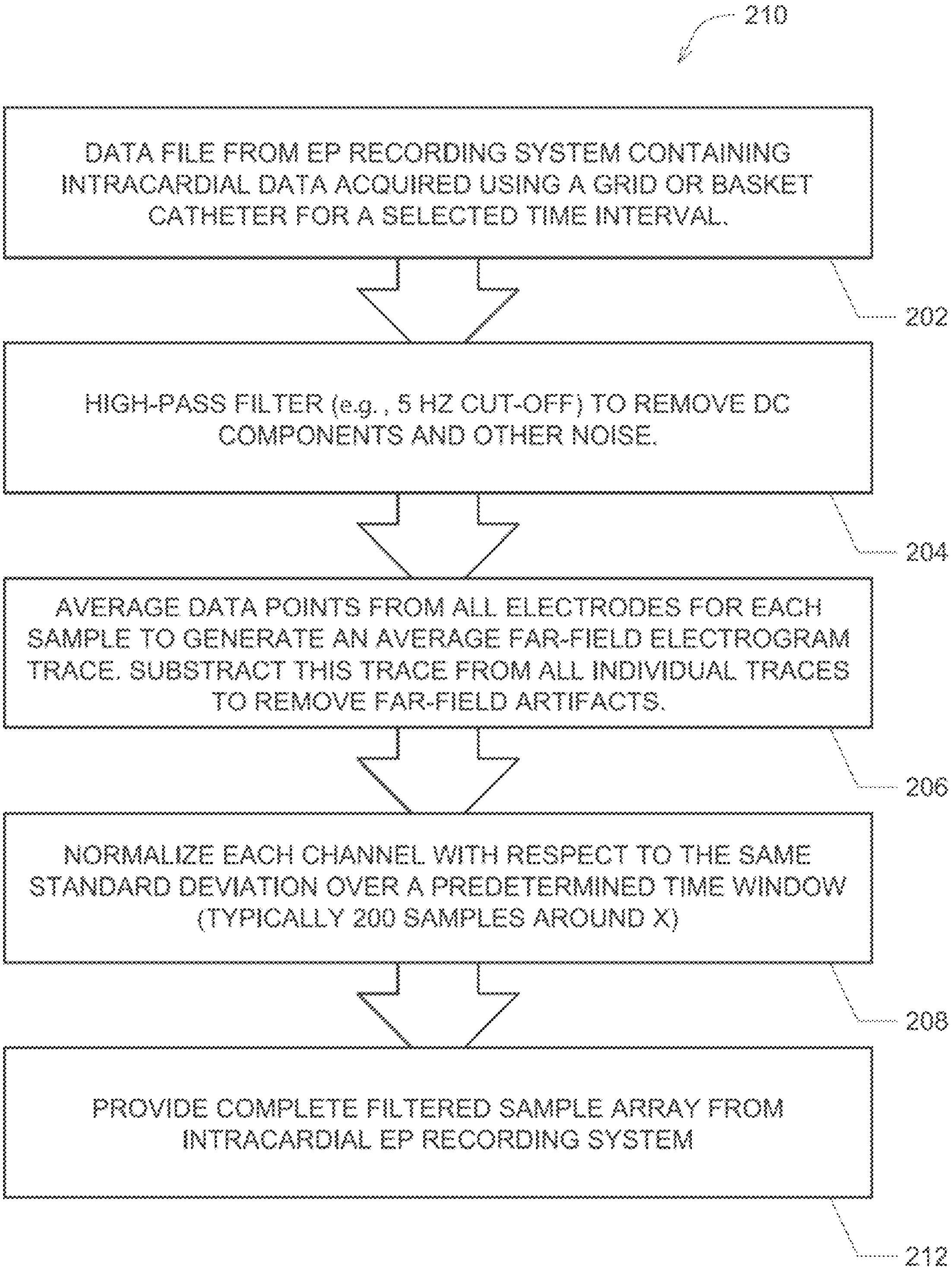
FIGS. 6(*a*) through 6(*c*) show details regarding one embodiment of method or algorithm 200 shown in FIG. 4.
Figure 6B:
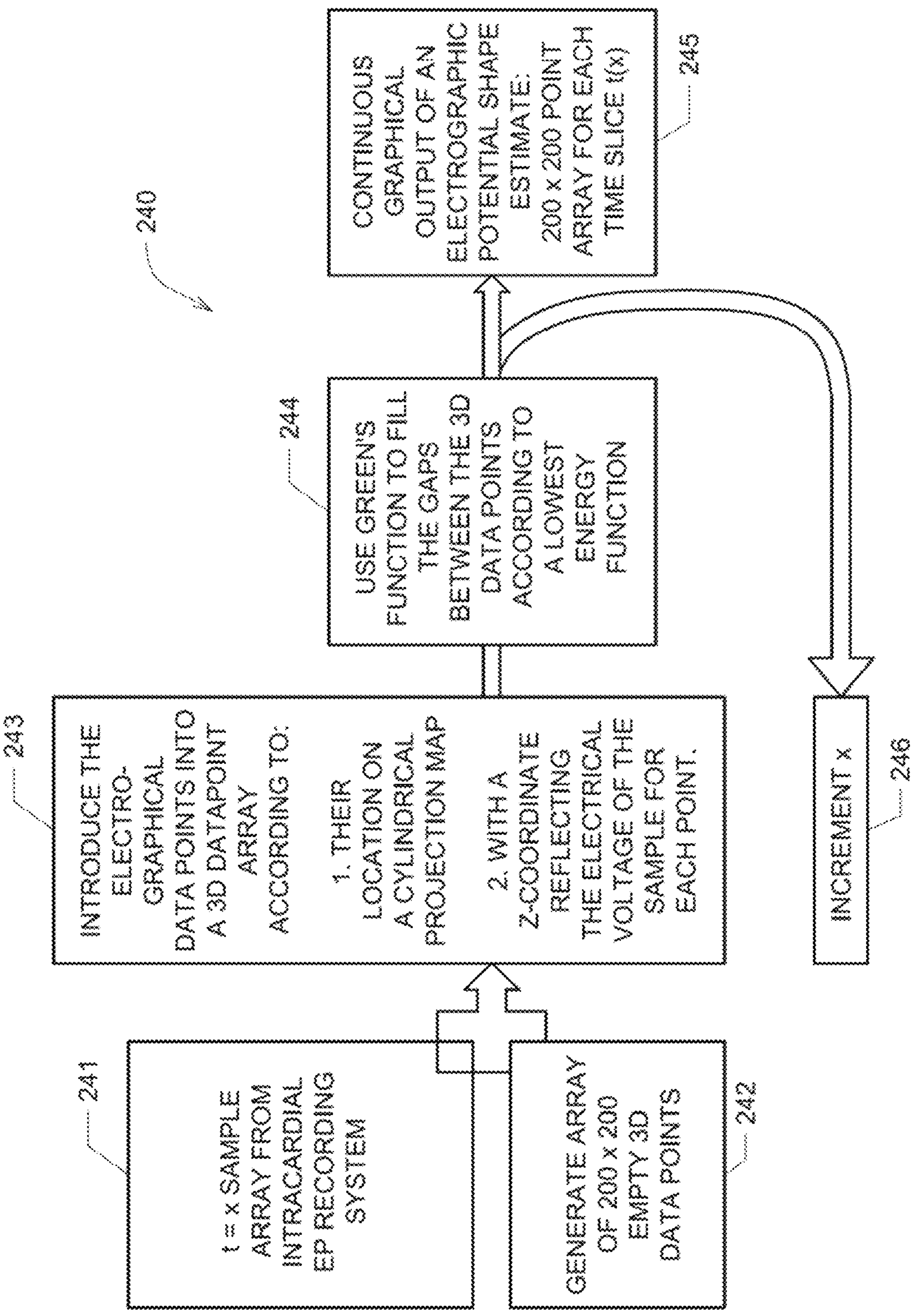
Figure 6C:
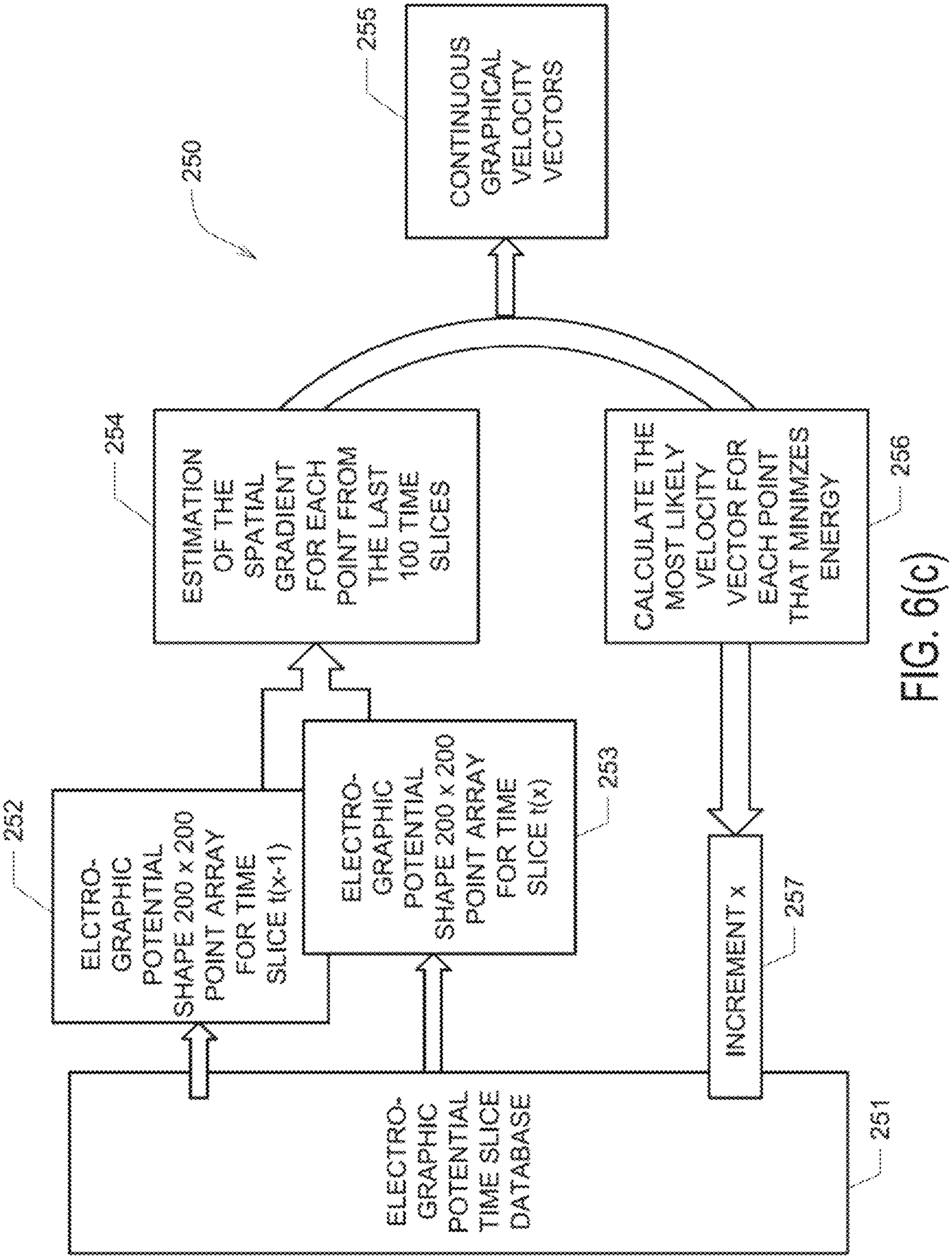
Figure 7A:
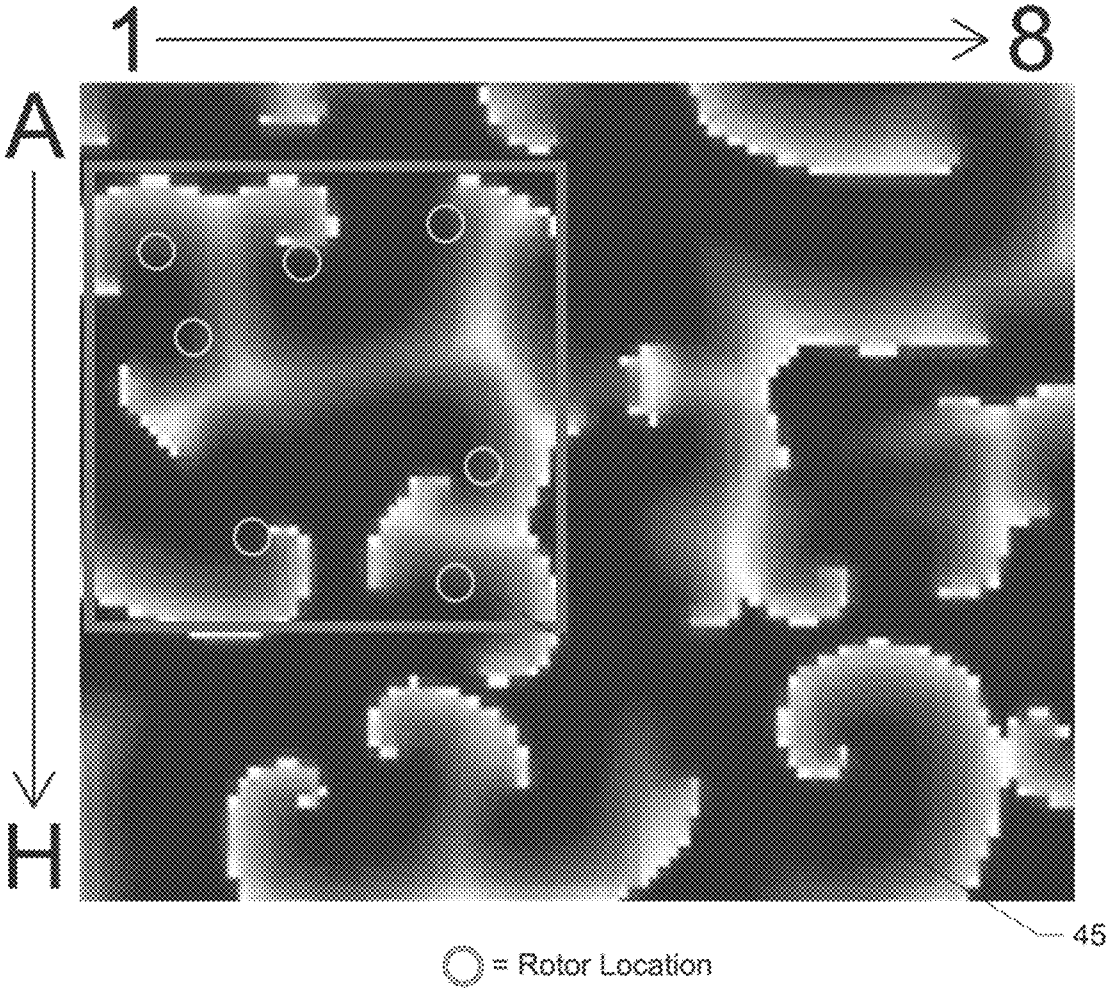
FIGS. 7(*a*) through 7(*j*) show the results of processing simulated atrial cardiac rhythm disorder data in accordance with one embodiment of method or algorithm 200.
Figure 7B:
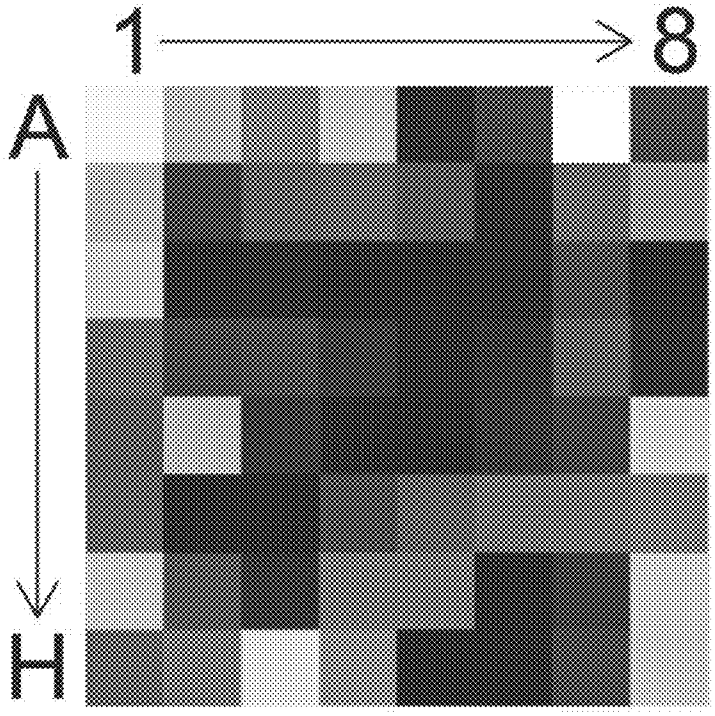
Figure 7C:
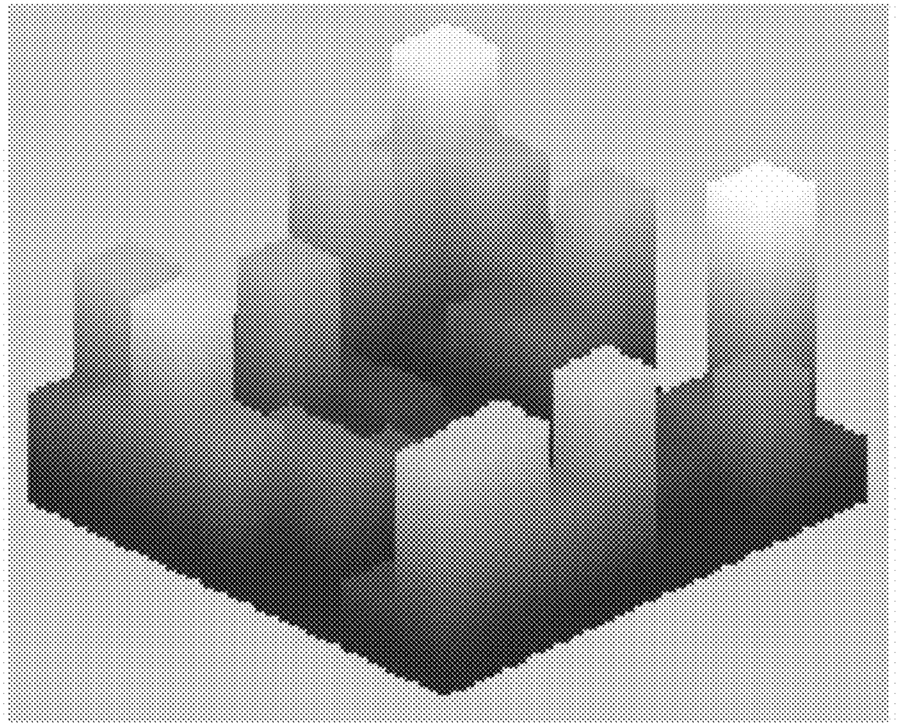
Figure 7D:
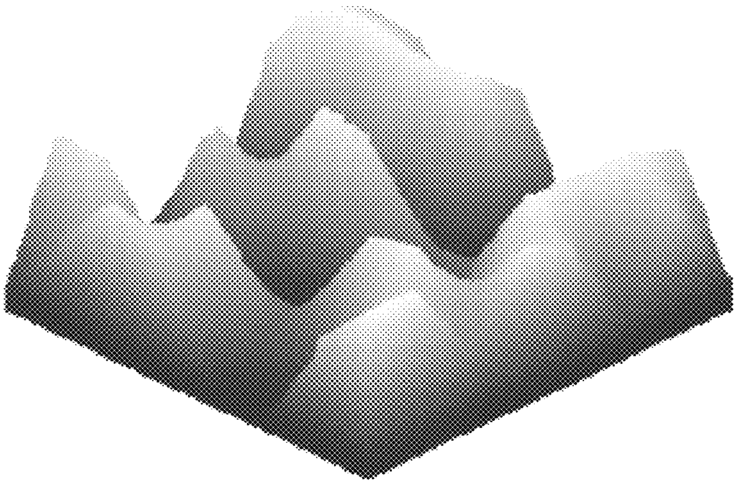
Figure 7E:
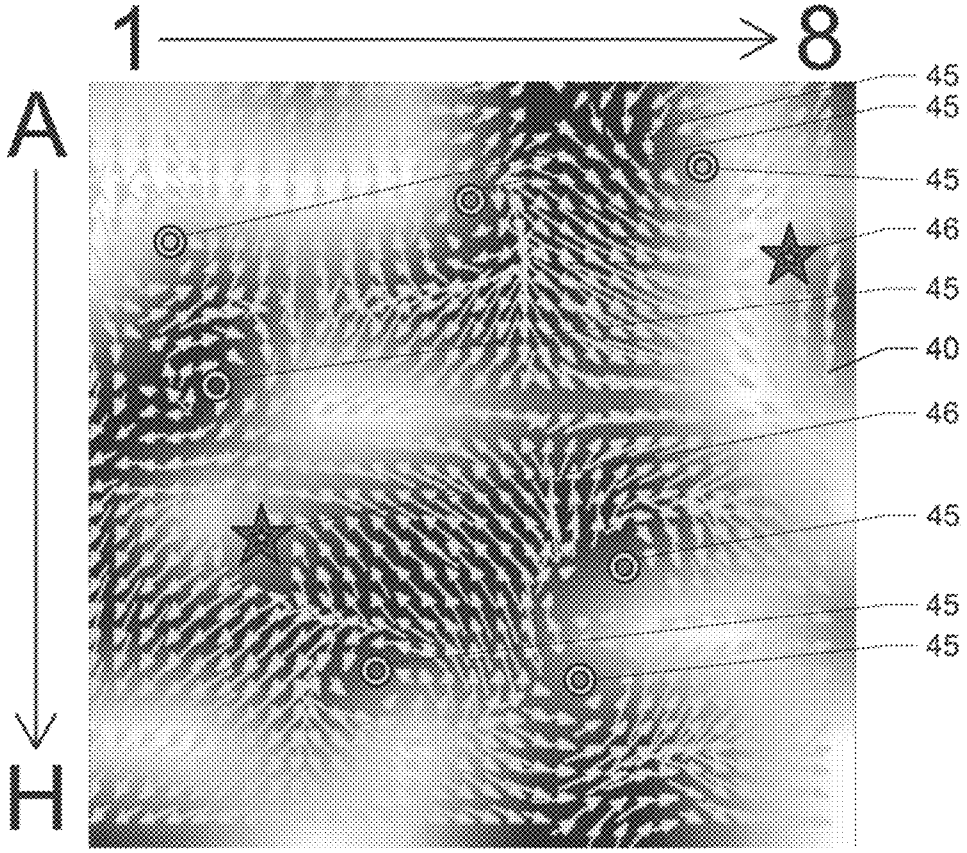
Figure 7F:
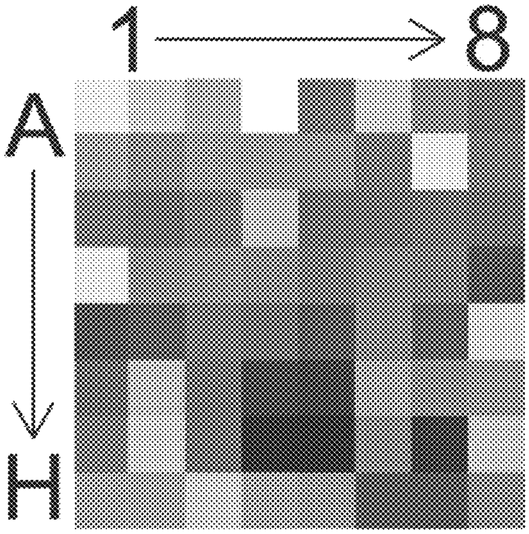
Figure 7G:
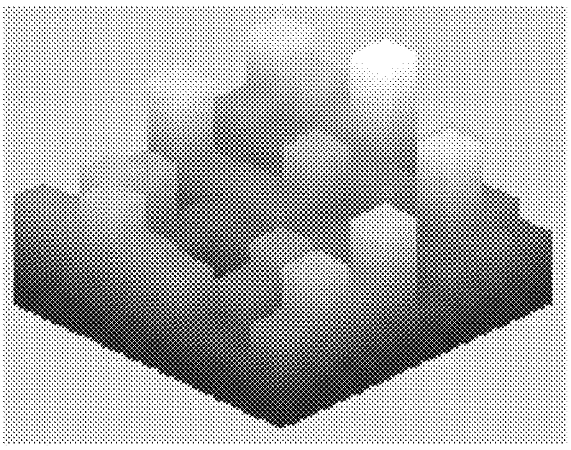
Figure 7H:
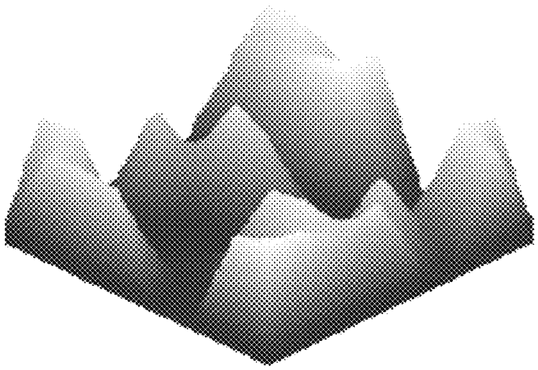
Figure 7I:
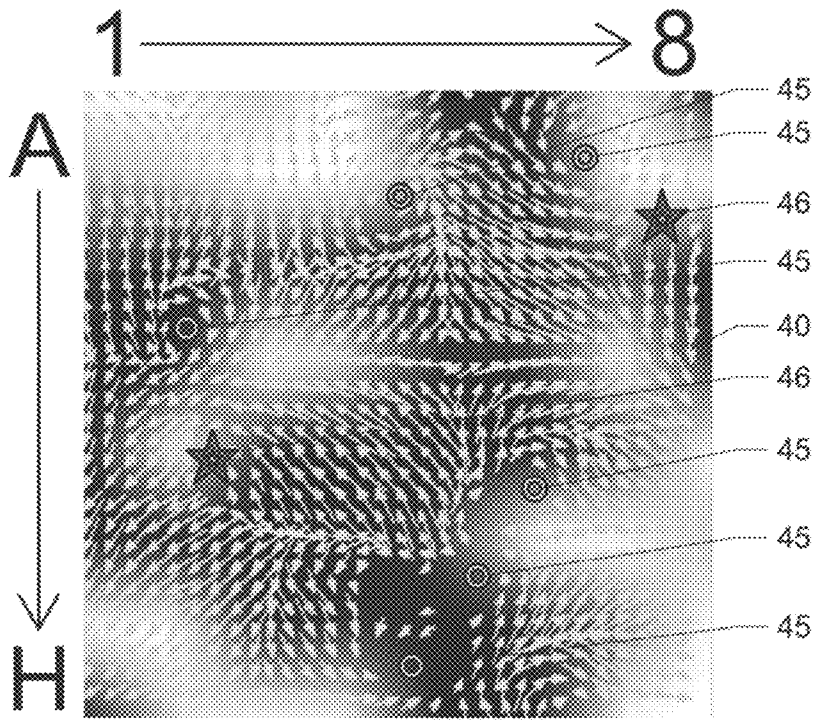
Figure 7J:
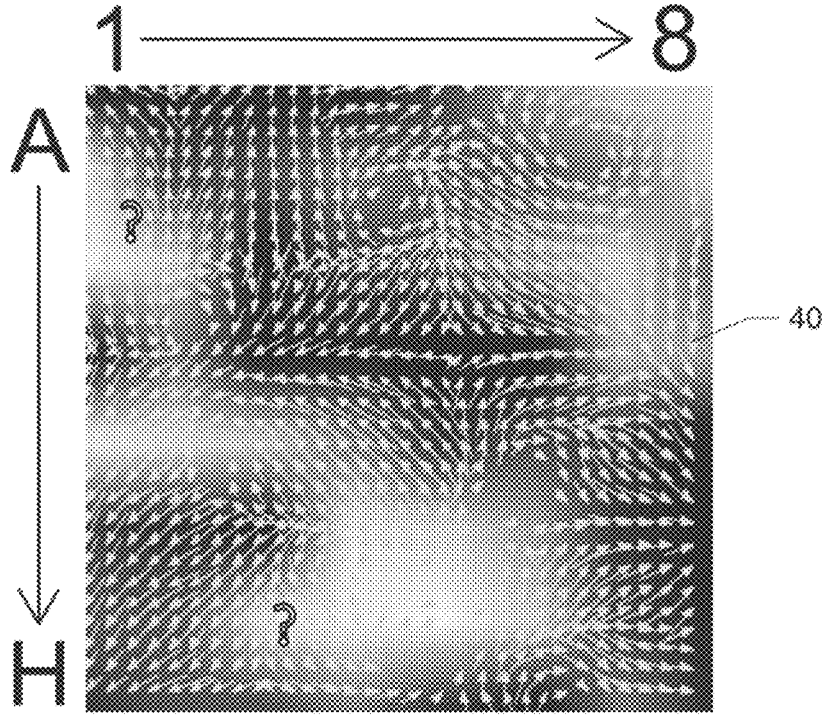

Referring now to FIGS. 6(*a*), 6(*b*) and 6(*c*), and with further reference to FIG. 4, there are shown some of the individual steps corresponding to the three main steps 230, 240 and 250 carded out according to one embodiment of algorithm 200 disclosed and described herein.

FIG. 6(*e*) shows one embodiment of steps 202 through 212 of main stop 210 of FIG. 4 ("normalized/adjust amplitudes, filter electrogram signals). In FIG. 6(*a*), step 202 is shown as comprising receiving a data file corresponding to the EP recording of electrogram signals from a basket or other type of EP recording catheter positioned in a patient's heart 10. The lime interval over which such electrogram signals are recorded inside the patient's heart 10 may, of course, vary according to, among other things, the requirements of the examination that is to be performed, and/or the suspected or known cardiac rhythm disorder from which the patient suffers. Illustrative, but non-limiting, examples of such time intervals range between about a second and one minute at more. Bad or poor fidelity traces or electrograms may be selectively removed or edited at this stage.

At step 204, a high-pass filter is applied to the acquired EP data to remove DC offsets, as well as other undesirable low-frequency noise. In one embodiment, a 5 Hz high-pass filter is applied, although other filters, including band-pass filters, are contemplated, including, but not limited to, 10 Hz high-pass filters, 5-20 Hz band-pass fillers, and 5-50 Hz band-pass filters. Notch- and tow-pass filtering may also be applied in step 204. Henning, trapezoidal and other digital filtering and/or Fast Fourier Transform (FFT) filtering techniques may also be applied.

At step 208, an average far-field electrogram signal is generated by stacking and averaging all electrogram traces. In the case of atrial EP recordings, the resulting estimate of a far-field ventricular depolarization is subtracted from each trace individual ty, thereby removing or at least reducing the far-field component therefrom.

At step 208, the amplitudes of individual filtered electrogram signals are normalized with respect to a given standard deviation occurring over a predetermined lime window (e.g., a moving window of 200 samples around a time value "x").

At step 212, a complete filtered sample stray from the grid or basket catheter is provided as an output from first main stop 210.

Referring now to FIG. 6(*b*), there is shewn one embodiment of the second main step 230 of algorithm 200 shown in FIG. 4 (processing amplitude-adjusted electrogram signals across the 2D or 3D representation, map or grid to generate a plurality of three-dimensional electrogram surfaces, one surface being generated for each selected or predetermined discrete time or time mice).

In FIG. 6(*b*), second main step 240 is shown as including steps 241 and 243, which according to one embodiment are performed in parallel or near-parallel. At step 241, digitally sampled and processed electrogram signals from step 212 of FIG. 6(*a*) are provided, and at step 242 an array of 200×200 empty 3D data points are generated, which correspond to the 2D or 3D representation, map or grid which is to be generated (or has already been generated). In one embodiment, such a representation, map or grid is formed by making a cylindrical projection representation, map or grid that corresponds to an approximate estimate or calculated map of the region of the patient's myocardial wall where the electrogram signals were acquired and measured (see step 243) by catheter 110.

Positional data from imaging or navigation system 70 can be provided at this stage to improve the positional accuracy of the individual locations with in such grid where electrogram signals were acquired. In one embodiment, for each time slice or sampled time, a Z-value or electrical potential corresponding to the normalized, adjusted and/or filtered measured voltage of each individual electrogram is assigned a location in the representation, map or grid.

At step 244, Green's function, or another suitable surface generating algorithm, is used to generate a surface of Z-values for each time slice or sampled time (more about which is said below), in one embodiment, the surface corresponding to the Z-values is smoothed.

At step 245, the calculated surface corresponding to each time slice or sampled time is provided as an output, with, for example, a 200×200 array of smoothed data points corresponding to the smoothed surface being provided for each lime slice or sampled time. Note that in some embodiments the intervals at which time slices are selected, or the individual time slices themselves, may be predetermined, or may be selected automatically or by the user.

FIG. 6(*c*) shows step 250 corresponding to one embodiment of the third main step of FIG. 4 (processing the plurality of three-dimensional electrogram surfaces generated across a 2D or 3D map through time to generate a velocity vector map, for example by means of the optical flow analysis and estimation techniques and methods, such those described and disclosed elsewhere herein. In FIG. 6(*c*), third man step 250 is shown as including step 251, which in one embodiment entails sequentially accessing the individual surfaces generated for selected time slices and/or discrete times in step 240. At steps 252 and 253, adjacent time slices ae analyzed and processed sequentially, in stop 254, a spatial gradient corresponding to each point of the representation, map or grid is calculated say over, for example, the last 100 time slices. At step 255, a continuous graphical output of calculated flow vectors can be provided as a real-time or near-real-time output. At step 256, the most likely flow vector magnitude (or velocity) and direction for each point that minimizes energy is calculated. At step 257, X (or time) is incremented, and the foregoing calculations are repeated and refined, the final output of which is a vector velocity map of the type shown, by way of non-limiting example, in FIGS. 5(*g*), 7(*e*), 7(*i*), 7(*j*), 7(*k*), 7(*l*), 8, 9, 10(*a*), 10(*c*), and 10(*e*).

FIGS. 7(*a*) through 7(*j*) show the result of processing simulated atrial cardiac rhythm disorder data using the methods and techniques described and disclosed above, where the concept of analyzing complex rotor structures was applied to a data set of simulated data. The simulated data shown in FIG. 7(*a*) primarily comprised stable active and passive rotors, as described in Carrick et al. in "Prospectively Quantifying the Propensity for Atrial Fibrillation: A Mechanistic Formulation," R. T. Carrick. P. S. Spector et al.; Mar. 13, 2013, the entirety of which is hereby incorporated by reference herein. From Carrick, et al.'s video corresponding to the foregoing publication, and referring now to FIG. 7(*a*), stable rotor data were recorded for a frame delineated by the indicated blue square, where there am seven rotors. The recording was accomplished using the luminance of the video frame in an 8×8 matrix with an 8-bit signal depth, thereby to simulate electrogram signal data acquired using a conventional 64-electrode 8×8 basket catheter. The overall video composed 90 frames. All data shown in FIG. 7(*a*) were taken from frame 60. Signal amplitudes from frame 60 are shown in the chess field and box plots of FIGS. 7(*b*) and 7(*c*), respectively.

FIG. 7(*a*), 7 rotors are shown marked with circles within the rectangle. In FIG. 7(*b*), a box plot of 8×8 matrix amplitude is shown having amplitudes corresponding to frame 60. FIG. 7(*d*) shows the estimated wavefront or smoothed surface corresponding to flame 60. FIG. 7(*c*) shows the vector velocity map generated from the data corresponding to FIG. 7(*a*) (which was generated on the basis of all 90 frames or times slices). Reference to FIG. 7(*e*) shows that seven active rotors (marked with circles 45) are apparent, as are two passive rotors (marked with stars 46).

Referring now to FIGS. 7(*b*) and 7(*c*), it will be seen that the 2D and 3D box patterns shown therein provide rough estimates of the spatial wavefronts shown in FIG. 7(*a*). In FIG. 7(*d*), however, the or net data shown in FIG. 7(*a*) are reproduced fairly accurately, and also provide a good input to the vector velocity map of FIG. 7(*e*) (which nicely reveals the 7 active rotors visible in FIG. 7(*a*)). The vector arrows 40 in FIG. 7(*e*) not only show the rotational centers of the individual rotors, but also show that active rotors indicated by circles 45 are driving sources of the wave fronts because the calculated vectors of the active rotors always point centrifugally away from the rotor centers. In contrast, the two stars 46 shown in FIG. 7(*e*) indicate the locations of passive rotors or flow turbulences that, while circular in shape, have centripetal vector directions to at least on one side of the rotor centers associated therewith.

Discrimination between active and passive rotors is critical to making proper therapeutic decisions regarding the delivery of ablation therapy, which should only target structures underlying the drivers of atrial fibrillation (namely, active rotors only, and not passive rotors).

Next, the effects of typical artifact disturbances on the signals of the 64 channels of data shown in FIGS. 7(*a*) through 7(*d*) were determined by introducing simulated variable amplitude DC-offset noise and artifacts into the electrogram signals. The objective was to test the extent to which such artifacts and noise might impair or disable the ability of algorithm 200 to detect rotors in the data.

FIGS. 7(*f*) and 7(*g*) show the same box plot data as FIGS. 7(*b*) and 7(*c*), respectively, but with the foregoing-described superimposed and introduced artifacts. That it, FIGS. 7(*f*) and 7(*g*) show the chess field and box plots of the disturbed electrogram signals corresponding to frame 60. After filtering and normalization in slap 210, the original rotor structure shown in FIG. 7(*a*) once again becomes visible in FIG. 7(*h*) following completion of the main second step 240 of the algorithm.

Upon applying smoothed surface calculations and fitting (as shown in FIG. 7(*i*)), algorithm 200 is seen to detect only five of the seven active rotors shown in FIG. 7(*a*). One additional active rotor, however, was detected at a different location (see FIG. 7(*i*)).

The largest variation in results was seen at positions where the introduction of the artifacts and noise reduced relative amplitude values by the greatest amount, as indicated by the white areas shown in FIG. 7(*j*). The white areas shown in FIG. 7(*j*) were generated by using the sliding-window amplitude-adjusted electrogram signal techniques described above, where electrograms processed using siding-window techniques were used to generate the image background (including the white areas) shown in the velocity vector map of FIG. 7(*j*). The white areas in FIG. 7(*j*) thus correspond to low amplitude areas potentially indicative of valve defects or artifacts, loose electrode contact, and/or areas of fibrosis in the patient's myocardium. It is Important to point out that the low-amplitude areas shown in while in the various velocity vector maps presented herein are not calculated using Green's function or optical flow data processing techniques, instead, and as described above, these low-amplitude regions or areas may be detected by assessing the relative amplitudes of electrogram signals in step 210.

In the white areas of FIG. 7(*j*) the resulting velocity vector map snows that the active rotors indicated therein are slightly moved closer together than in FIG. 7(*i*), and on the left center side of FIG. 7(*j*) two rotors appearing in FIG. 7(*i*) are revealed as a single active rotor in FIG. 7(*j*), FIGS. 7(*a*) through 7(*j*) show that there are limits to the resolution that can be achieved using a conventional 8×8 array of sensing electrodes 82 in a basket catheter having standard interelectrode spacing. Thus, higher electrode densities and more recording channels could increase the resolution and accuracy of the results obtained using algorithm 200.

After confirming that algorithm 200 was capable of detecting complex rotor structures accurately in a patient's myocardium—even in the presence of strong artifacts and noise—algorithm 200 was applied to different time portions of the actual patient data shown in FIG. 5(*b*) so as to test further the algorithm's efficacy and accuracy. A velocity vector map corresponding to data acquired between 4,700 milliseconds and 5,100 milliseconds in the original EU recording of FIG. 5(*b*) is shown in FIG. 8(*a*).

Figure 8A:
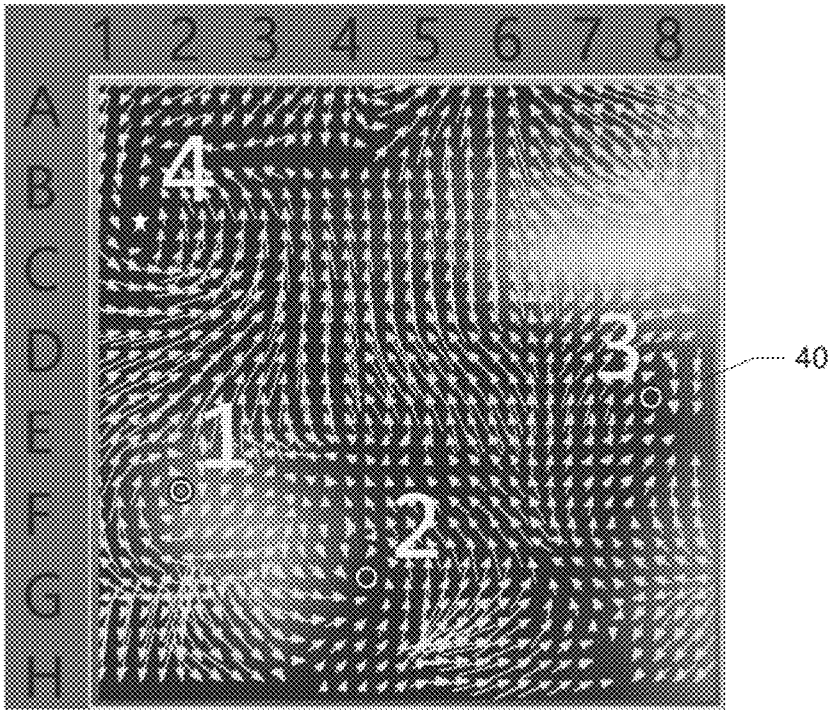
FIGS. 8(*a*) and 8(*b*) show velocity vector maps generated from actual patent data using different time windows and method or algorithm 200.
Figure 8B:
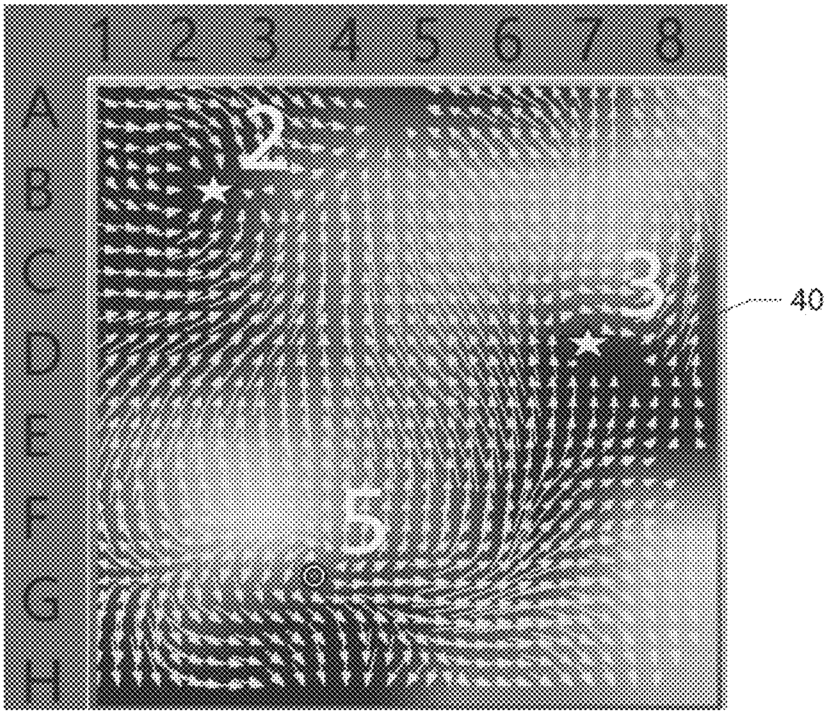

As shown in FIG. 8(*a*), four rotors indicated by circles 1, 2 and 3 and a star 4 were detected. Circles 1 and 2 in FIG. 8(*a*) appear to denote active rotors that are interacting with one another. Circle (3) in FIG. 8(*a*) may be an active rotor, but exhibits some centripetal components. Star 4 in FIG. 8(*a*) clearly corresponds to a passive rotor. Next, a velocity vector map corresponding to the same data set for data acquired between samples 0 seconds and 400 milliseconds was generated, the results of which are shown in FIG. 8(*b*). Differences between the results shown in FIGS. 8(*a*) and 8(*b*) permit a deeper insight into the true rotor structure of this patient's myocardium, as best shown in FIG. 8(*b*). In the earlier time interval (0 msec, to 400 msec.) of FIG. 8(*b*), the two associated rotors 1 and 2 shown in FIG. 8(*a*) are not yet active, while there is only a single active rotor 5 in FIG. 8(*b*) located between the positions of rotors 1 and 2 shown in FIG. 8(*a*). Rotors 1 and 2 in FIG. 8(*b*) show up at slightly different positions, but now appear clearly as passive rotors representing likely turbulences generated at the border of a mitral valve artifact.

Thus, a health care professional can Select differing time windows over which to apply algorithm 200 to an EP mapping data set as a means of gaining a better understanding of the behavior of active and passive rotors, fibrotic regions, areas affected by valve defects or artifacts, breakthrough points and areas or defects that are at work in the patient's myocardium. The velocity vector maps generated by algorithm 200 permit a health care professional to identify such cardiac rhythm disorders in a patient's myocardium with a degree of precision and accuracy that has heretofore not been possible using conventional FU mapping and intravascular basket or spline catheter devices and methods.

Figure 9:
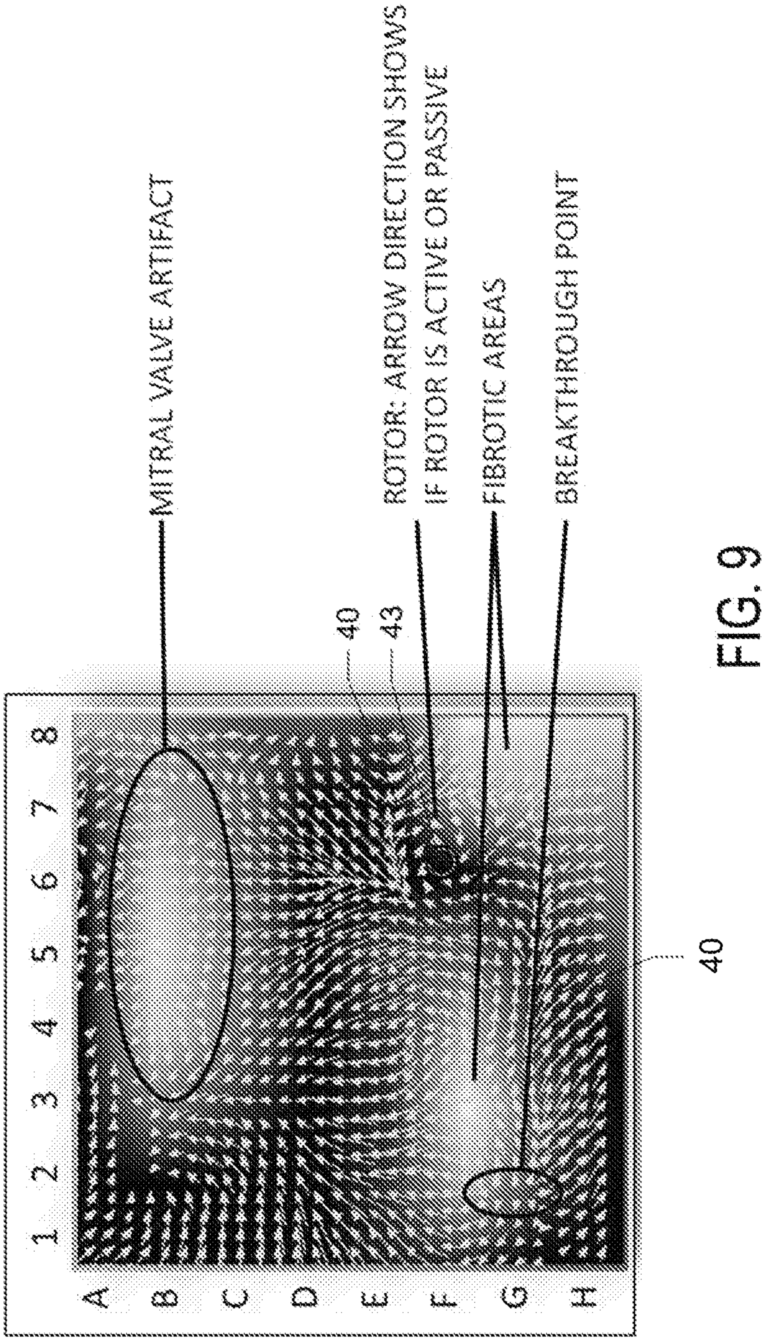
FIG. 9 shows another vector velocity map generated from actual patient data using method or algorithm 200, and FIGS. 10(*a*) through 10(*d*) show further results obtained using actual patient data.
Figure 10A:
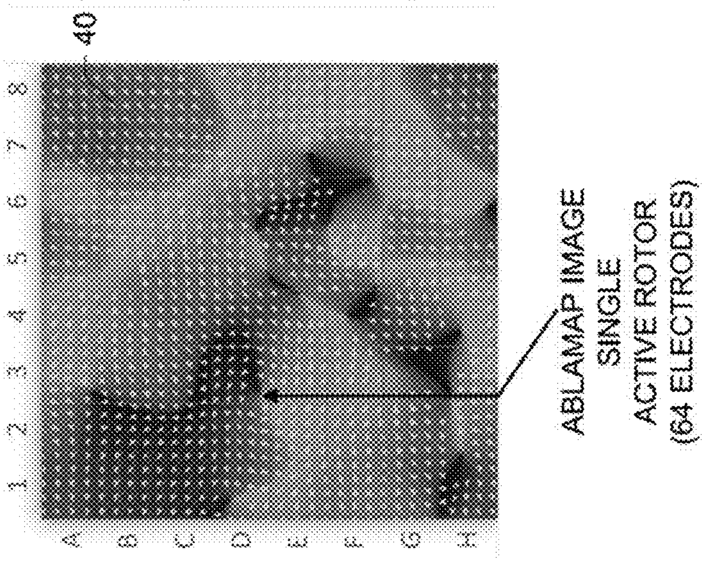
Figure 10B:
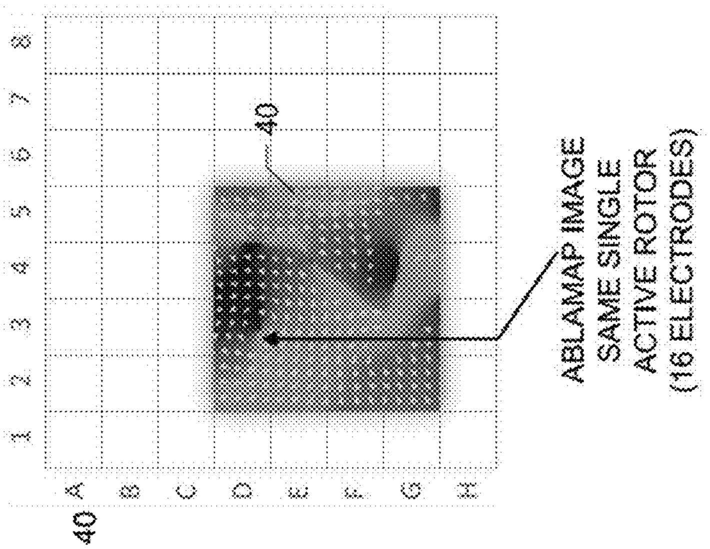
Figure 10C:
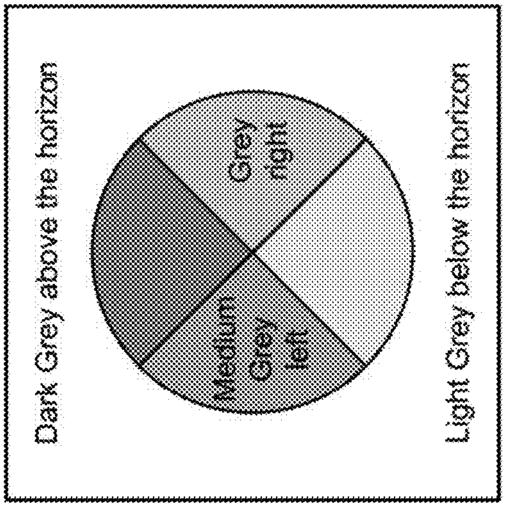
Figure 10D:
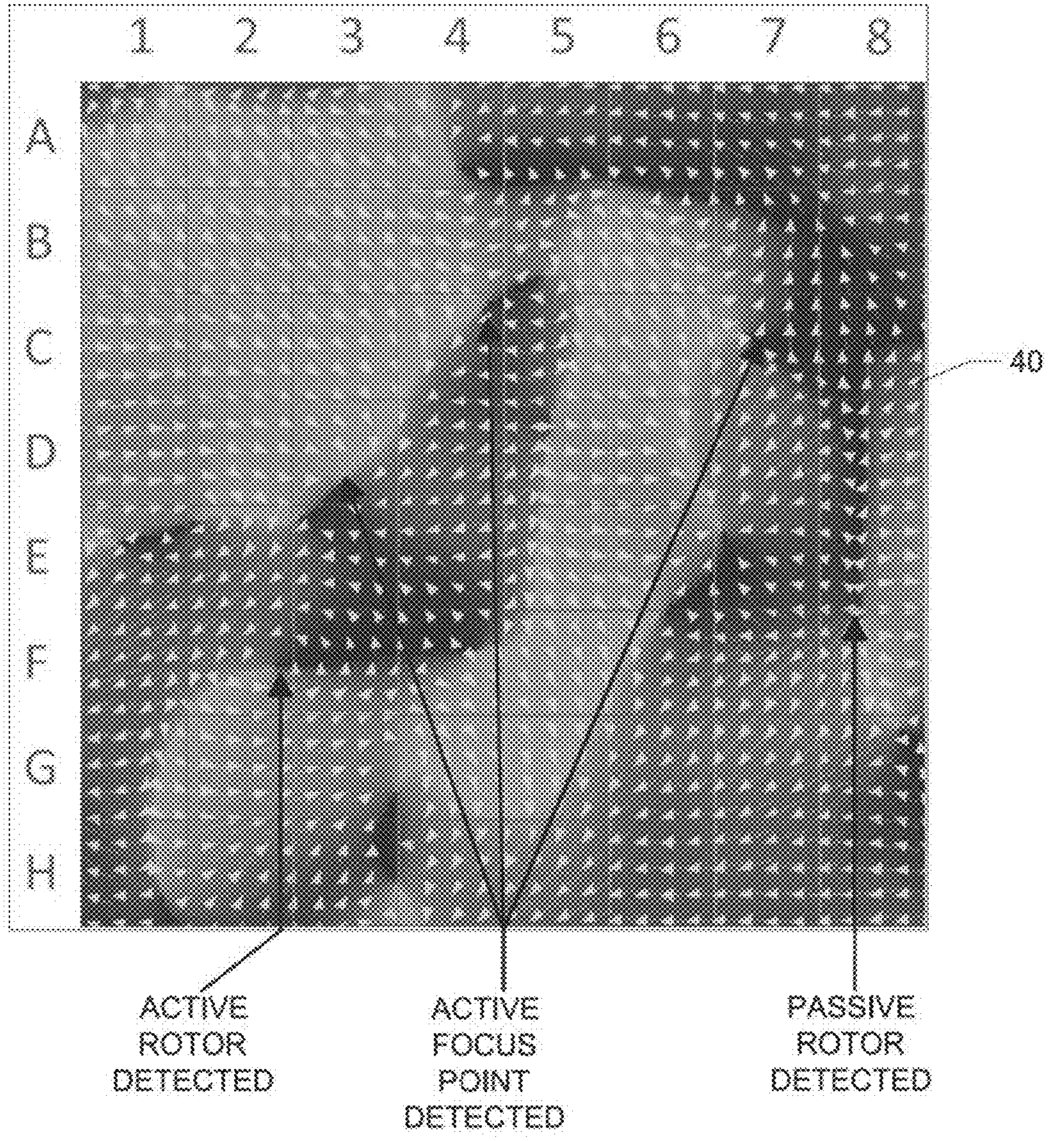

Referring now to FIG. 9, there it shown another example of a vector velocity map generated from actual patient data using algorithm 200. In FIG. 9, the arrows 40 correspond to action potential wavefront velocity vectors, which as illustrated have differing magnitudes and directions associated herewith. As shown in FIG. 9, various cardiac rhythm defects and disorders become apparent as a result of the generated vector velocity map. The defects and disorders revealed by the vector velocity map of FIG. 9 include an active rotor (where the active rotor propagation direction is indicated in the bottom tight of FIG. 9 by a circular arrow 43 rotating in a clockwise or centrifugal direction), a breakthrough point in the bottom left of FIG. 9, fibrotic areas indicted by low-amplitude white areas in the lower portion of FIG. 9, and a mitral valve defect indicted by the white area in the upper portion of FIG. 9.

Referring now to FIGS. 10(*a*) through 10(*d*), there are shown further results obtained using the actual patient data. The raw data corresponding to FIGS. 10(*a*) through 10(*d*) were acquired from a single patient's right atrium using a 64-electrode basket catheter and corresponding EP mapping recording system. Data were acquired at a 1 millisecond rate over a time period of 60 seconds in all 64 channels. FIGS. 10(*a*) and 10(*b*) correspond to one selected 2 second time window, and FIG. 10(*d*) corresponds to another time window from the same data set. FIG. 10(*c*) shows the greyscale-schemes employed in FIGS. 10(*a*), 10(*b*), and 10(*d*).

The vector velocity map of FIG. 10(*a*) generated using algorithm 200 clearly reveals an active rotor located at chess board position DIE, 2/3. The vector velocity map of FIG. 10(*b*) was also generated using algorithm 200, but using data acquired from only 16 electrodes 82 in grid D-C, 2-5. As shown in FIG. 10(*b*), the active rotor evident in FIG. 10(*a*) is nearly equally evident in FIG. 10(*b*) despite the significantly more sparse data grid employed to produce the velocity vector map. These remarkable results obtained using a sparse electrode grid are due in large part to the robustness, stability and accuracy of algorithm 200, as it has been applied to electrographical flow problems.

FIG. 10(*d*) shows another example of results obtained using algorithm 200 and EP mapping data obtained from the same patient as in FIGS. 10(*a*) and 10(*b*), but over a different time window. Note also that FIG. 10(*d*) shows that algorithm 200 has successfully detected one active rotor (at chess board location F2/3), three active focus points, and one passive rotor (at chess board location F8).

It will now be seen that algorithm 200 provides not only rotational direction information, but also provides high-resolution spatial information regarding the presence and location of rotors despite the use of sparse electrode grid spacing. Rotors can also move over time in a patient's myocardium, even during the time interval over which EP mapping is being carried out. The increased spatial and temporal resolution of algorithm 200 permits such shifts in rotor location to be detected.

In some embodiments, and as described above, multiple or different types of EP mapping and ablation catheters can be used sequentiality or at the same time to diagnose and/or treat the patient. For example, a 64-electrode CONSTELLATION basket catheter can be used for EP mapping in conjunction with a PENTARAY16- or 20-electrode EP mapping catheter, where the PENTARAY EP mapping catheter is used to zero in on, and provide fine detail regarding, a particular region of the patient's myocardium that the basket catheter has revealed as the location of a source of a cardiac rhythm disorder or irregularity. In addition, catheter 110 or any other EP mapping catheter used in system 100 may be configured to provide ablation therapy (in addition to EP mapping functionality). The various catheters employed in system 100 may also include navigation elements, coils, markers and/or electrodes so that the precise positions of the sensing, pacing and/or ablation electrodes inside the patient's heart 10 are known. Navigational data can be employed by computer 300 in algorithm 200 to provide enhanced estimates of the locations of the electrodes in the representations, maps or grids generated thereby, which in turn increases the accuracy and efficacy of the resulting velocity vector maps generated to algorithm 200.

In another embodiment, computing device/system 300 is operably connected to a storage medium such as a hard drive or non-volatile memory located in, or operably connected to, data acquisition device 140, where computing device 300 is configured to trigger an external switch operably connected to data acquisition device 140 which permits the upload of conditioned electrogram signal data from data acquisition device 140 to computing device 300. According to such a configuration, computing device 300 and data acquisition device 140 can remain galvanically isolated from one another, and the need to physically swap USD memory sticks between data acquisition device 140 and computing device 300 is eliminated. This, in turn, permits system 100 to operate more efficiently and quickly, and to provide vector velocity maps to the health care professional in near-real-time while the EP mapping procedure is being carried out within the patient's heart 10.

The various systems, devices, components and methods described and disclosed herein may also be adapted and configured for use in electrophysiological mapping applications other than those involving the interior of a patient's heart. These alternative applications include EP mapping and diagnosis of a patient's epicardium, a patient's spinal cord or other nerves, or a patents brain or portions thereof.

It will now be seen that the various systems, devices, components and methods disclosed and described herein are capable of detecting with considerable accuracy and precision the locations of sources of cardiac rhythm disorders in a patient's heart.

What have been described above are examples and embodiments of the devices and methods described and disclosed herein. It is of course, not possible to describe every conceivable combination of components or methodologies for purposes of describing the invention, but one of ordinary skill in the art will recognize that many further combinations and permutations of the devices and methods described and disclosed herein are possible. Accordingly, the devices and methods described and disclosed herein are Intended to embrace all such alterations, modifications and variations that fait with in the scope of the appended claims. In the claims, unless otherwise indicated, the article a is to refer to "one or more than one."

The foregoing outlines features of several embodiments so that those skilled in the art may better understand the detailed description set forth herein. Those skilled in the art will now understand that many different permutations, combination and variations of hearing aid 10 fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those ski led in the art should also realize that such equivalent constructions do not depart from the spirit and scope or the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems, both in the use of electrophysiological mapping systems and in the use of cardiac ablation systems.

The invention claimed is:

1. A method of one or more of estimating, defecting and/or determining one or more locations of at least one source of at least one cardiac rhythm disorder and/or irregularity in a patient's heart using at least one computing device and a display operably connected thereto, wherein the at least one computing device comprises at least one nontransitory computer readable medium configured to store instructions executable by at least one processor for estimating, detecting and/or determining the at least one source and at least one location of the at least one cardiac rhythm disorder and/or irregularity in the patient's heart, the method comprising: (a) receiving a plurality of electrogram signals from an array of a plurality of electrodes positioned in or on a patient; (b) in the computing device, assigning spatial or areal positions to each of the plurality of electrodes and to each of the individual electrogram signals corresponding to each electrode; (c) for each or selected discrete times over which the plurality of electrogram signals are being processed, processing the plurality of electrogram signals in the computing device to generate a plurality of data sets or two-dimensional or three-dimensional electrogram surfaces corresponding at least partially to the electrode positions; (d) processing the plurality of electrogram surfaces or data sets through time in the computing device to generate a vector map or visualization corresponding at least partially to the electrode spatial or areal positions, the vector map or visualization being configured to display to a user one or more estimated, detected and/or determined locations of the sites, sources or origins of the cardiac rhythm disorders and/or irregularities within the patient's heart, and (e) displaying to the user on the display the vector map or visualization.

2. The method of claim 1, further comprising normalizing and/or adjusting amplitudes of the plurality of electrogram signals in the data acquisition device before processing the plurality of electrogram signals in the computing device to generate the plurality of two- or three-dimensional electrogram surfaces or data sets corresponding at least partially to the electrode positions.

3. The method of claim 1, wherein one surface or data set is generated for each time when the plurality of two- or three-dimensional electrogram surfaces or data sets is generated.

4. The method of claim 1, wherein at least portions of the electrogram surfaces or data sets generated by the computing device are configured to correspond to estimated wave shapes or wavefront.

5. The method of claim 1, wherein the electrogram surfaces or data sets are generated by the computing device using Green's function.

6. The method of claim 1, wherein the vector map or datasets generated by the computing device comprise arrows or colors representative of directions of electrical potential propagation.

7. The method of claim 1, wherein the vector map or data sets generated by the computing device comprise arrows or colors having attributes representative of velocities of electrical potential propagation.

8. The method of claim 1, wherein the vector map or data sets generated by the computing device are configured to display to the user a focal point at the location, site or origin.

9. The method of claim 1, wherein the velocity vector map is generated by the computing device using at least one optical flow analysis technique.

10. The method of claim 9, wherein the at least one optical flow analysis techniques selected from the group consisting of a Horn-Schunck method.

11. The method of claim 1, wherein the plurality of electrogram signals are processed by the computing device to generate an averaged electrogram signal, and the averaged electrogram signal is subtracted from each of the individual electrogram signals to generate artifact- or far-field adjusted individual electrogram signals.

12. The method of claim 11, wherein the artifact-adjusted individual electrogram signals are processed by the computing device with a high-pass filter to remove DC offsets.

13. The method of claim 12, wherein the high-pass filter applied by the computing device removes frequencies below between about 5 Hz and about 20 Hz.

14. The method of claim 1, wherein interpolated or estimated values are generated by the computing device for positions in between the spatial or areal positions of the electrodes or their corresponding electrogram signals.

15. The method of claim 1, wherein a representative amplitude value is generated by the computing device for each individual electrogram signal, and the representative amplitude value generated for each electrogram signal is stored for later use in image backgrounds that show low signal amplitude areas, the low signal amplitude areas being indicative of one or more of valve artifacts, poor electrode contact, and fibrotic areas of the heart.

16. The method of claim 1, wherein interpolated or estimated values are generated by the computing device for positions in between the spatial or areal position of the electrodes or their corresponding electrogram signals.

17. The method of claim 1, wherein the spatial or areal positions of the electrodes or their corresponding electrogram signals are modified by the computing device based upon navigational or positional data corresponding to measured or sensed actual electrode positions.

18. The method of claim 17, wherein the navigational data are provided to the computing device by one or more of a medical navigation system, a computed tomography scanner, a magnetic resonance image scanner, and an X-ray fluoroscopy system.

19. The method of claim 1, further comprising an ablation system comprising an ablation catheter, the ablation catheter being configured for ablating the patient's heart at the location of the and source of the cardiac rhythm disorder indicated by the vector map.

20. A system for one or more of estimating, detecting and/or determining one or more locations of at least one source of at least one cardiac rhythm disorder and/or irregularity in a patient's heart using at least one computing device and a display operably connected thereto, wherein the at least one computing device comprises at least one nontransitory computer readable medium configured to store instructions executable by at least one processor for estimating, detecting and/or determining the at least one source and at least one location of the at least one cardiac rhythm disorder and/or irregularity in the patient's heart, the system being configured to: (a) receive a plurality of electrogram signals from an array of a plurality of electrodes positioned in or on a patient; (b) assign spatial or areal positions to each of the plurality of electrodes and to each of the individual electrogram signals corresponding to each electrode; (c) for each or selected discrete times over which the plurality of electrogram signals are being processed, process the plurality of electrogram signals to generate a plurality of data set or two-dimensional or three-dimensional electrogram surfaces corresponding at least partially to the electrode positions; (d) process the plurality of electrogram surfaces or data sets through time to generate a vector map or visualization corresponding at least partially to the electrode spatial or areal positions, the vector map or visualization being configured to display to a user one or more estimated, detected and/or determined locations of the sites, sources or origins of the cardiac rhythm disorders and/or irregularities within the patient's heart, and (e) display to the user on the display the vector map or visualization.

21. The system of claim 20, wherein the system is further configured to normalize and/or adjust amplitudes of the plurality of electrogram signals in the data acquisition device before processing the plurality of electrogram signals in the computing device to generate the plurality of two- or three-dimensional electrogram surfaces or data sets corresponding at least partially to the electrode positions.

22. The system of claim 20, wherein one surface or data set is generated by the computing device for each time when the plurality of two- or three-dimensional electrogram surfaces or data sets is generated.

23. The system of claim 20, wherein at least portions of the electrogram surfaces or data sets generated by the computing device are configured to correspond to estimated wave shapes or wavefront.

24. The system of claim 20, wherein the electrogram surfaces or data sets are generated by the computing device using Green's function.

25. The system of claim 20, wherein the vector map or data sets generated by the computing device comprise arrows or colors representative of directions of electrical potential propagation.

26. The system of claim 20, wherein the vector map or data sets generated by the computing device comprise arrows or colors having attributes representative of velocities of electrical potential propagation.

27. The system of claim 20, wherein the vector map or data sets generated by the computing device are configured to display to the user a focal point at the location, site or origin.

28. The system of claim 20, wherein the velocity vector map is generated by the computing device using at least one optical flow analysis technique.

29. The system of claim 28, wherein the at least one optical flow analysis technique is a Horn-Schunck method.

30. The system of claim 20, wherein the plurality of electrogram signals are processed by the computing device to generate an averaged electrogram signal, and the averaged electrogram signal is subtracted from each of the individual electrogram signals to generate artifact- or far-field adjusted individual electrogram signals.

31. The system of claim 30, wherein the artifact-adjusted individual electrogram signals are processed by the computing device with a high-pass filter to remove DC offsets.

32. The system of claim 31, wherein the high-pass filter applied by the computing device removes frequencies below between about 5 Hz and about 20 Hz.

33. The system of claim 20, wherein interpolated or estimated values are generated by the computing device for positions in between the spatial or areal positions of the electrodes or their corresponding electrogram signals.

34. The system of claim 20, wherein a representative amplitude value is generated by the computing device for each individual electrogram signal, and the representative amplitude value generated for each electrogram signal is stored for later use in image backgrounds that show low signal amplitude areas, the low signal amplitude areas being indicative of one or more of valve artifacts, poor electrode contact, and fibrotic areas of the heart.

35. The system of claim 20, wherein interpolated or estimated values are generated by the computing device for positions in between the spatial or areal position of the electrodes or their corresponding electrogram signals.

36. The system of claim 20, wherein the spatial or areal positions of the electrodes or their corresponding electrogram signals are modified by the computing device based upon navigational or positional data corresponding to measured or sensed actual electrode positions.

37. The system of claim 20, wherein the navigational data are provided to the computing device by one or more of a medical navigation system, a computed tomography scanner, a magnetic resonance image scanner, and an X-ray fluoroscopy system.

38. The system of claim 20, further comprising an ablation system comprising an ablation catheter, the ablation catheter being configured for ablating the patient's heart at the location of the and source of the cardiac rhythm disorder indicated by the vector map.

* * * * *